United States Patent
Mortis et al.

(10) Patent No.: US 12,350,481 B2
(45) Date of Patent: *Jul. 8, 2025

(54) PRESSURE UNLOADING LEFT VENTRICULAR ASSIST DEVICE AND METHODS FOR ASSISTING A HUMAN HEART

(71) Applicant: Kardiatec SA, Athens (GR)

(72) Inventors: Chris A. Mortis, Charlotte, NC (US); Jay W. Mason, Reno, NV (US); John Nanas, Ntrafi (GR)

(73) Assignee: KARDIATEC SA, Athens (GR)

( * ) Notice: Subject to any disclaimer, the term of this patent is extended or adjusted under 35 U.S.C. 154(b) by 124 days.

This patent is subject to a terminal disclaimer.

(21) Appl. No.: 18/069,959

(22) Filed: Dec. 21, 2022

(65) Prior Publication Data

US 2023/0372695 A1    Nov. 23, 2023

Related U.S. Application Data

(62) Division of application No. 16/779,603, filed on Feb. 1, 2020, now Pat. No. 11,565,102.

(Continued)

(51) Int. Cl.
*A61N 1/362*  (2006.01)
*A61M 1/00*   (2006.01)
(Continued)

(52) U.S. Cl.
CPC ........ *A61M 60/148* (2021.01); *A61M 60/152* (2021.01); *A61M 60/274* (2021.01);
(Continued)

(58) Field of Classification Search
None
See application file for complete search history.

(56) References Cited

U.S. PATENT DOCUMENTS

| 2,925,830 A | 2/1960 | Kautrowitz |
| 4,004,298 A | 1/1977 | Freed |

(Continued)

OTHER PUBLICATIONS

Christos D. Kontogiannis et al. "Continuous internal counterpulsation as a bridge to recovery in acute and chronic heart failure" World Journal of Transplantation, Mar. 24, 2016, pp. 115-124, vol. 6, issue 1, Baishideng Publishing Group, Inc.

(Continued)

*Primary Examiner* — Jon Eric C Morales
(74) *Attorney, Agent, or Firm* — McNees Wallace & Nurick LLC

(57) ABSTRACT

An implantable pump includes a rigid housing with an oblate spheroid shape and having an inner chamber divided by a movable elastomeric membrane into a gas sub-chamber which is connectible through a drive line to an external pneumatic source, and a blood sub-chamber which is connectible through a graft assembly to an anatomical heart. The housing includes a blood port opening oriented at an angle and at the upper apex of the housing and connected to the blood sub-chamber, and a gas port opening to the gas sub-chamber that is situated at a lower apex of the housing. The pump is provided with a drive line that includes a gas conduit and a heart sensor, the drive line connectible to a drive system that is capable of delivering gas flow through the drive line gas conduit in response to signals driven by the heart sensor.

20 Claims, 13 Drawing Sheets

Related U.S. Application Data

(60) Provisional application No. 62/800,208, filed on Feb. 1, 2019.

(51) Int. Cl.
| | |
|---|---|
| *A61M 60/148* | (2021.01) |
| *A61M 60/152* | (2021.01) |
| *A61M 60/274* | (2021.01) |
| *A61M 60/405* | (2021.01) |
| *A61M 60/515* | (2021.01) |
| *A61M 60/837* | (2021.01) |
| *A61M 60/857* | (2021.01) |
| *A61M 60/859* | (2021.01) |
| *A61M 60/861* | (2021.01) |
| *A61M 60/88* | (2021.01) |

(52) U.S. Cl.
CPC ........ *A61M 60/405* (2021.01); *A61M 60/515* (2021.01); *A61M 60/837* (2021.01); *A61M 60/857* (2021.01); *A61M 60/859* (2021.01); *A61M 60/861* (2021.01); *A61M 60/88* (2021.01); *A61M 2205/0216* (2013.01); *A61M 2205/3306* (2013.01); *A61M 2210/127* (2013.01); *A61M 2230/06* (2013.01)

(56) References Cited

U.S. PATENT DOCUMENTS

| | | |
|---|---|---|
| 4,051,840 A | 10/1977 | Kantrowitz et al. |
| 4,092,742 A | 6/1978 | Kantrowitz et al. |
| 4,222,127 A | 9/1980 | Donachy et al. |
| 4,573,997 A | 3/1986 | Wisman et al. |
| 4,630,597 A | 12/1986 | Kantrowitz et al. |
| 4,634,422 A | 1/1987 | Kantrowitz et al. |
| 4,692,148 A | 9/1987 | Kantrowitz et al. |
| 4,704,120 A | 11/1987 | Slonina |
| 4,733,652 A | 3/1988 | Kantrowitz et al. |
| 4,809,681 A | 3/1989 | Kantrowitz et al. |
| 4,810,246 A | 3/1989 | Frisch et al. |
| 4,913,700 A | 4/1990 | Kantrowitz et al. |
| 4,938,766 A | 7/1990 | Jarvik |
| 5,139,508 A | 8/1992 | Kantrowitz et al. |
| 5,169,379 A | 12/1992 | Freed et al. |
| 5,242,415 A | 9/1993 | Kantrowitz et al. |
| 5,308,319 A | 5/1994 | Ide et al. |
| 5,332,403 A | 7/1994 | Kolff |
| 5,403,273 A | 4/1995 | Lindsay |
| 5,667,485 A | 9/1997 | Lindsay |
| 5,761,019 A | 6/1998 | Kroll |
| 5,833,619 A | 11/1998 | Freed et al. |
| 5,833,655 A | 11/1998 | Freed et al. |
| 5,904,666 A | 5/1999 | DeDecker et al. |
| 5,931,648 A | 8/1999 | Del Canizo |
| 6,007,559 A | 12/1999 | Arkans |
| 6,042,532 A | 3/2000 | Freed et al. |
| 6,048,353 A | 4/2000 | Freed et al. |
| 6,132,363 A | 10/2000 | Freed et al. |
| 6,146,325 A | 11/2000 | Lewis et al. |
| 6,216,570 B1 | 4/2001 | Freed |
| 6,217,541 B1 | 4/2001 | Yu |
| 6,468,200 B1 | 10/2002 | Fischi |
| 6,471,633 B1 | 10/2002 | Freed |
| 6,503,228 B1 | 1/2003 | Li et al. |
| 6,508,787 B2 | 1/2003 | Erbel et al. |
| 6,511,412 B1 | 1/2003 | Freed et al. |
| 6,735,532 B2 | 5/2004 | Freed et al. |
| 6,808,484 B1 | 10/2004 | Peters et al. |
| 6,846,294 B2 | 1/2005 | Rastegar et al. |
| 6,863,670 B2 | 3/2005 | Zheng et al. |
| 6,889,082 B2 | 5/2005 | Bolling et al. |
| 6,969,349 B1 | 11/2005 | Spence et al. |
| 6,981,942 B2 | 1/2006 | Khaw et al. |
| 7,048,702 B2 | 5/2006 | Hui |
| 7,066,874 B2 | 6/2006 | Riebman et al. |
| 7,125,376 B2 | 10/2006 | Viole et al. |
| 7,144,365 B2 | 12/2006 | Bolling et al. |
| 7,273,446 B2 | 9/2007 | Spence |
| 7,357,771 B2 | 4/2008 | Peters et al. |
| 7,374,531 B1 | 5/2008 | Kantrowitz |
| 7,458,929 B2 | 12/2008 | Bolling et al. |
| 7,468,029 B1 | 12/2008 | Robertson, Jr. |
| 7,468,050 B1 | 12/2008 | Kantrowitz |
| 7,479,102 B2 | 1/2009 | Jarvik |
| 7,481,760 B2 | 1/2009 | Rastegar et al. |
| 7,513,863 B2 | 4/2009 | Bolling et al. |
| 7,513,864 B2 | 4/2009 | Kantrowitz et al. |
| 7,544,160 B2 | 6/2009 | Gross |
| 8,092,364 B2 | 1/2012 | Spence |
| 8,323,174 B2 | 12/2012 | Jeevanandam et al. |
| 9,054,773 B2 | 6/2015 | Kerselaers |
| 11,565,102 B2 * | 1/2023 | Mortis ................ A61M 60/859 |
| 2004/0152945 A1 | 8/2004 | Kantrowitz et al. |
| 2005/0148810 A1 | 7/2005 | Riebman et al. |
| 2006/0030747 A1 | 2/2006 | Kantrowitz |
| 2006/0199993 A1 | 9/2006 | Riebman et al. |
| 2007/0026032 A1 | 2/2007 | Kantrowitz |
| 2007/0173682 A1 | 7/2007 | Smith et al. |
| 2007/0265490 A1 | 11/2007 | Smith et al. |
| 2008/0281147 A1 | 11/2008 | Kantrowitz |
| 2008/0281412 A1 | 11/2008 | Smith et al. |
| 2009/0131741 A1 | 5/2009 | Kantrowitz |

OTHER PUBLICATIONS

Christos Kontogiannis et al. "Effects of a novel implantable counterpulsation assist device on left entricular mechanoenergetics: comparison with the intra-aortic balloon pump in a porcine model of acute heart failure", Heart Failure and Cardiomyopathies: Surgical Approaches/LVADs, JACC Apr. 5, 2016, vol. 67, issue 13, presentation No. 1137-080, University of Athens, School of Medicine, Athens, Greece.

John V. Terrovitis et al. "Superior Performance of a Paraaortic Counterpulsation Device Compared to the Intraaortic Balloom Pump", World Journal of Surgery, Dec. 2003, pp. 1311-1316, vol. 27, issue 12, Societe Internationale de Chirurgie.

Stavros G. Drakos et al. "Reverse remodeling during long-term mechanical unloading of the left ventricle" Journal of Molecular and Cellular Cardiology, 2007, pp. 231-242, vol. 43, issue 3, Elsevier Inc.

PCT International Preliminary Report on Patentability issued to Application No. PCT/US2020/016299 dated Jul. 27, 2021.

PCT Notification of Transmittal of International Search Report and The Written Opinion of the International Searching Authority of the Declaration, issued to Application No. PCT/US2020/016299 dated Jul. 31, 2020.

Third Office Action issued to Chinese counterpart Application No. 202080011662.2 dated Jan. 22, 2025.

* cited by examiner

PRESSURE UNLOADING LEFT VENTRICULAR ASSIST DEVICE AND METHODS FOR ASSISTING A HUMAN HEART

RELATED APPLICATIONS AND PRIORITY

This application is a divisional of and claims the benefit of U.S. Nonprovisional application Ser. No. 16/779,603 filed Feb. 1, 2020, which claims priority to U.S. Provisional Application No. 62/800,208, filed Feb. 1, 2019, the entirety of which are incorporated herein by reference.

BACKGROUND OF THE INVENTION

Heart failure represents a major public health challenge with high morbidity, mortality, and cost. Prevalent in 2% of the adult population in developed countries, heart failure is singled out as the only heart disease entity with escalating prevalence and a current annual healthcare expenditure of ~$31 billion in the United States, estimated to reach $70 billion in 2030. Advanced heart failure accounts for the majority of resources spent to manage heart failure, with one-year mortality up to ~80%. Patients with advanced heart failure face limited access to donor hearts for cardiac transplantation, and mechanical support devices are often a last resort.

Chronic mechanical circulatory support with left ventricular assist devices (LVADs) have been employed to "bridge" end-stage heart failure patients to transplantation or as a permanent "destination" therapy. In rare instances, LVAD support has been seen to reverse cardiac remodeling to the point where a minority of patients can be weaned from the device after partial restoration of cardiac function, thus avoiding both transplant and long-term use of assistive technology. Unfortunately, clinically available LVADs bypass the left ventricle and produce profound ventricular unloading, to the point that the failing left ventricle is rendered ineffective to generate adequate pressure to surpass the arterial pressure generated by the LVAD itself. In addition, pulsatility of flow appears to be important for promoting myocardial recovery, while currently used continuous-flow LVADs are associated with a threefold decrease in recovery rate compared with older-generation pulsatile alternatives. In sum, clinically available LVADs unload and assist the left ventricle at the cost of severely depressing native left ventricular function; this prolonged functional depression could promote fibrosis and compromise the heart's innate potential for recovery.

In view of the variety of problems with clinically available LVAD technology, there is a clinical need for assistive technology that can provide the benefits of bridge to transplant and destination therapy and can preserve native left ventricular function and pulsatitlity to optimize the chances for myocardial recovery.

To address these needs of cardiac recovery induced by mechanical unloading, this disclosure provides a novel pressure unloading LVAD (PULVAD), which is a novel implantable counterpulsation assistive pump designed to unload the failing heart while preserving both left ventricular systolic activity and pulsatility.

SUMMARY OF THE INVENTION

In various embodiments, the disclosure provides a novel implantable counterpulsation LVAD, designed to provide ventricular unloading by augmentation of left ventricle performance and retention of pulsatility.

In a first embodiment, an implantable pump is provided. The implantable pump includes a rigid housing with an oblate spheroid shape and defining an inner chamber divided by a movable elastomeric membrane into an air sub-chamber which is connectible through a drive line to an external pneumatic source, and a blood sub-chamber which is connectible through a graft assembly to an anatomical heart, the housing including a blood port opening to the blood sub-chamber, the blood port adjacent an upper apex of the housing. In some embodiments, the blood port is oriented at an angle that is in a range from about 20 degrees to about 50 degrees relative to a through axis of the oblate spheroid. In some other embodiments, the blood port is oriented at an angle that is about 0 degrees, or that is in a range from about 1 degree to about 20 degrees relative to a through axis of the oblate spheroid. The housing also includes a gas port opening to the gas sub-chamber, the gas port situated at a lower apex of the housing.

In some examples according to the first embodiment, one or both of the blood port and the gas port comprises an opening that is valveless.

In some examples according to the first embodiment, the elastomeric membrane has a shape that generally conforms to the inner chamber and the blood port and has an expansion volume that is less than a total volume of the chamber and the blood port. In some specific examples, the elastomeric membrane comprises a bulb section, a cylindrical neck, and a cuff that interfaces with the housing connector.

In some examples according to the first embodiment, the pump further includes a housing connector and a graft assembly. In some specific examples, the graft assembly comprises a graft conduit, a washer, and a graft connector. In some further examples, the graft connector is engagable with the housing connector by any one of threaded, snap fit, or quick connector.

In some examples according to the first embodiment, each of the blood portal and graft conduit having an internal surface, each such internal surface having essentially the same diameter at an interior surface interface therebetween.

In some examples according to the first embodiment, the blood port has a blood port axis that intersects a central axis through the rigid housing at an angle that is from about 0 to about 50 degrees. And in some examples according to the first embodiment, the gas port has an inner diameter in the range from about 1.5 mm to about 5 mm.

In a second embodiment, a drive line for a blood pump is provided. The drive line includes a pair of conduits that are contiguously connected over at least a portion a length of the drive line and are split apart at each of first and second ends of the drive line, the drive line further comprising a disc shaped circumferential flange positioned between the first and second ends and beyond a split between the pair of conduits, the pair of conduits comprising a gas conduit attachable at a first end to a gas port of an implantable pump, and a sensor conduit comprising a heart sensor for monitoring heart rhythm passed through the sensor conduit, the heart sensor comprising one or more of a plurality of electrodes and fiber optic sensors, the heart sensor attachable at a first end to a clinical subject, wherein each of the gas conduit and the sensor conduit is attachable at its second end to a drive system which is capable of delivering gas flow through the drive line gas conduit in response to signals driven by the heart sensor.

In a third embodiment, a system for assisting blood flow is provided. The system includes:

(a) an implantable pump comprising: a rigid housing with an oblate spheroid shape and defining an inner chamber divided by a movable elastomeric membrane into an air sub-chamber which is connectible through a drive line to an external pneumatic source, and a blood sub-chamber which is connectible through a graft assembly to an anatomical heart, the housing including a blood port opening to the blood sub-chamber, the blood port adjacent an upper apex of the housing. In some embodiments, the blood port is oriented at an angle that is in a range from about 20 degrees to about 50 degrees relative to a through axis of the oblate spheroid. In some other embodiments, the blood port is oriented at an angle that is about 0 degrees, or that is in a range from about 1 degree to about 20 degrees relative to a through axis of the oblate spheroid. The housing also including a gas port opening to the gas sub-chamber, the gas port situated at a lower apex of the housing;

(b) a housing connector affixed to the blood portal, and adapted to engage with a graft assembly;

(c) a graft assembly; and (d) a drive line comprising a gas conduit attachable at a first end to the gas port of the implantable pump, and a sensor conduit and a heart sensor passed therethrough for monitoring heart rhythm, the heart sensor attachable at a first end to a clinical subject, and each of the gas conduit and the sensor conduit a attachable at respective second ends to a drive system which is capable of delivering gas flow through the drive line gas conduit in response to signals driven by the heart sensor.

In some examples according to the third embodiment, the gas conduit and sensor conduit of the drive line are continuous at their connection to the drive system and are split in two prior to the attachment of the gas conduit to the gas port. In some specific examples, the sensor is selected from one or more of electrodes and fiber optic sensors. In a further example, the sensor comprises a plurality of electrodes.

In some examples according to the third embodiment, the gas conduit portion of the drive line includes a disc shaped circumferential flange.

In a fourth embodiment, a method for promoting blood flow is provided. The method includes the steps of:

(a) preparing a clinical subject for receiving an implantable device wherein the clinical subject has a thoracic cavity that includes a heart having a pericardium, an ascending aorta, a pulmonary artery, a superior vena cava, and left and right lungs;

(b) providing an implantable pump having a rigid housing with an oblate spheroid shape and having an inner chamber, the housing including a blood port opening to the inner chamber, the blood port adjacent an upper apex of the oblate spheroid In some embodiments, the blood port is oriented at an angle that is in a range from about 20 degrees to about 50 degrees relative to a through axis of the oblate spheroid. In some other embodiments, the blood port is oriented at an angle that is about 0 degrees, or that is in a range from about 1 degree to about 20 degrees relative to a through axis of the oblate spheroid. The housing also includes a gas port opening to the inner chamber, the gas port situated at a lower apex of the oblate spheroid and oriented normal to the thorough axis of the oblate spheroid, and the pump including an internal elastomeric membrane that generally conforms to the inner chamber and the blood port, and has an expansion volume that is less than a total volume of the chamber and the blood port;

(b) placing the implantable pump between the heart and the right lung of the clinical subject;

(c) partially clamping the ascending aorta of the clinical subject;

(d) providing a graft assembly that comprises a flexible graft conduit that includes a tissue attachment end and a pump attachment end that comprises a washer, and a graft connector;

(e) affixing the tissue attachment end of the flexible graft conduit to the partially clamped aorta;

(f) providing a drive line comprising a gas conduit attachable at a first end to the gas port of the implantable pump, the drive line further comprising a sensor conduit and a heart sensor passed therethrough, the heart sensor comprising one or more of a plurality of electrodes and fiber optic sensors, the heart sensor attachable at a first end to the clinical subject, wherein the second end of the gas conduit and a second end of the sensor conduit are attachable to a drive system for delivering gas flow through the drive line gas conduit in response to signals driven by the heart sensor, the drive line including a circumferential disc shaped flange;

(g) passing the drive line through an incision in the clinical subject with the flange abutting the incision;

(g) attaching the gas conduit to the gas port of the pump;

(h) placing each of the one or more of a plurality of electrodes and fiber optic sensors on an anatomical structure of the clinical subject selected from a portion of the pericardium, and within one of the pulmonary artery and the arterial artery;

(i) connecting the second ends of the conduits of the drive line to the drive system;

(j) affixing the implantable pump to the graft assembly by engagement between the graft connector and a housing connector on the blood port of the pump;

(k) removing the clamp from the clinical subject's aorta to permit blood flow from the heart into the blood pump via the graft and activating the drive system.

In some examples according to the fourth embodiment, the method does not require the employment of heart lung bypass.

In some examples according to the fourth embodiment, the blood port of the pump is oriented within the clinical subject's anatomy at angle to allow for anatomical fit and attachment to the ascending aorta while reducing the potential for kinking the graft conduit and superior vena cava compression.

In a fifth embodiment, an implantable device for assisting blood flow is provided. The device includes:

(i) a rigid housing having an oblate spheroid shape and comprising a blood portal section, a gas port section, the upper and gas port sections defining within the rigid housing a chamber having an oblate spheroid shape, (1) the blood portal section comprising a blood portal having a cylindrical shape and defining a through channel between an exterior of the rigid housing and the chamber, the blood portal having a blood portal axis that intersects a central axis through the upper and gas port sections of the rigid housing;

(2) the gas port section having an interior surface that includes a base, the base comprising a plurality of grooves and a gas port defining a gas flow conduit between the exterior of the rigid housing and the chamber, the gas port having a gas port axis that is normal to the rigid housing axis;

(ii) an elastomeric membrane comprising a bulb section, a cylindrical neck, and a cuff that interfaces with the housing connector, and having a shape that generally conforms to the chamber and the blood portal and having an expansion volume that is less than a total volume of the chamber and the blood portal, wherein the chamber includes a dead volume of from about 3 cc to about 10 cc when the elastomeric membrane is at its maximum expansion volume;

(iii) a housing connector affixed to the blood portal, and adapted to engage with a graft assembly; and (iv) a graft assembly comprising a graft conduit, a washer, and a graft connector engagable with the housing connector.

Other features and advantages of the present invention will be apparent from the following more detailed description of the preferred embodiment which illustrates, by way of example, the principles of the invention.

BRIEF DESCRIPTION OF THE DRAWINGS

The foregoing as well as other objects and advantages of the invention will become apparent from the following detailed description when considered in conjunction with the accompanying drawings, wherein like reference characters designate like parts throughout the several views, and wherein.

DETAILED DESCRIPTION OF THE INVENTION

Figure 2:
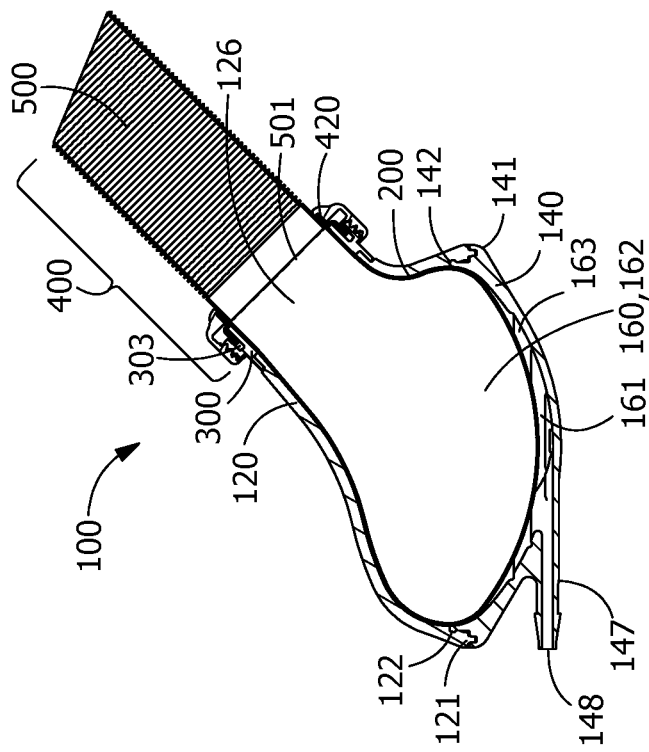
FIG. 2 is a side view in cross section of an implantable pump.

In accordance with the instant disclosure, an implantable pump device for assisting blood flow, more particularly a novel implantable counterpulsation LVAD designed to provide ventricular unloading with augmentation of left ventricular performance and retention of pulsatility for both short-term (e.g., 1 week) or long-term (e.g., 6 months) implantation.

As further described herein, the implantable device is advantageous in simplifying surgery and reducing damaging trauma to native heart tissue, in particular as compared with implantation of other assistive pumps. It is well known that clinically available intra-thoracic LVAD devices typically require heart lung bypass, whereas the surgical approach that may be employed to implant the disclosed pump eliminates the need for heart bypass during implantation. Further, because the device is not attached to or inserted into the heart, the device may be implanted via a sternotomy and a partial clamp of the aorta, whereby an anastomosis is used to attach the device's flexible graft to the partially clamped aorta, allowing for proper de-airing before releasing the aortic clamp. Thus, use of the disclosed device eliminates the need for a heart-lung machine, oxygenators, etc. typically used in open heart bypass. Further, the device only requires one anatomical connection to the aorta. This allows for the device to simply be turned off, and after appropriate preparation, burying subcutaneously the cropped ends of the gas port tube and electrodes without having to re-operate to explant the device. Further still, implantation of the device deliberately avoids any coring or damage to cardiac tissue which is typical with most LVAD implantations. Indeed, most other mainstream LVAD's connect with the apex of the ventricle, requiring a surgical incision of the heart muscle, and they involve the use of electrodes implanted into cored areas of the heart muscle. The instant device is affixed to the ascending aorta, without any damage to the heart muscle, and the electrode leads, when employed, are affixed using myocardial leads attached to the pericardium. Use of the instant device allows for the potential to recover the native function of the heart.

Further advantages of the device relate to its design, including how the device is designed to fit between the heart and the right lung and how the orientation of the blood port on the pump is angled to allow for anatomical fit and attachment to the aorta while reducing the potential for kinking the graft connector and superior vena cava compression. And the device does not incorporate any valves. Instead, the blood flows into and out of the device along the same path. This approach increases washing of the blood contacting surface of the device, minimizing stasis and reducing the potential for thrombus formation. And the device has essentially no moving parts other than a polyurethane membrane that deforms elastically in response to fluid movement on the respective gas and blood sides of the membrane. In addition, the instant device is unique in the number of electrodes that are used to sense the cardiac cycle and the area placed on the pericardium. Currently, five electrodes are placed on the pericardium of the heart to provide the signal for triggering the device. The multiple locations in the pericardium as opposed to one on the epicardium allows for more reliable signal detection and does not damage the epicardial layer of the heart. And, the device incorporates a novel driveline that delivers both electrical signals and pneumatic power to the device. The driveline exits through the abdominal wall and incorporates a flexible flange that helps to stabilize the exit site and reduce the potential for tract formation and exit site infection. And, the device is uniquely designed to be driven by most commercial IABP drivers, while other LVADs require expensive, proprietary, dedicated drivers. These and other advantages are as described herein.

As shown in the examples, below, the disclosed implantable pump exhibits significant differences compared to conventional LVADs which make it particularly attractive as a bridge to myocardial recovery. First, the device provides partial left ventricular pressure unloading and promotes a favorable hemodynamic condition of markedly reduced afterload and physiologically adjusted decreased preload; this favorable hemodynamic condition enables concurrent improvement of native left ventricular function. In contrast, clinically used LVADs markedly decrease left ventricular preload (driving native left ventricular function toward the bottom left of the Frank-Starling curve), while maintaining excessive afterload (generated by the LVAD itself). In this way, conventional LVADs unload the left ventricle at the cost of suppressing native left ventricular function, which could compromise recovery and promote fibrosis. Second, PULVAD support produces pulsatile flow, which is associated with higher rates of recovery compared to currently used continuous-flow LVADs. Third, the disclosed device offers a relatively simple and safe implantation/explantation technique without the need for either extracorporeal circulation or destruction of cardiac muscle, which are adverse features of typical LVAD insertion and removal. Fourth, the wide availability of driving consoles (the PULVAD is driven by standard IABP consoles) renders the PULVAD a broadly accessible therapeutic approach that could be readily implemented in most hospitals. Fifth, the absence of complex electromechanical parts and valves should (at least from a theoretical standpoint) result in reduced risk for thrombus formation and LVAD-associated complications.

FIGS. 1-19, which are now referenced, illustrate various aspects of the present invention and the manner in which they are assembled each having like reference numerals refer to like components according to the drawing and the key to reference numerals provided herein.

Implantable Pump 100 Components and System

Figure 1:
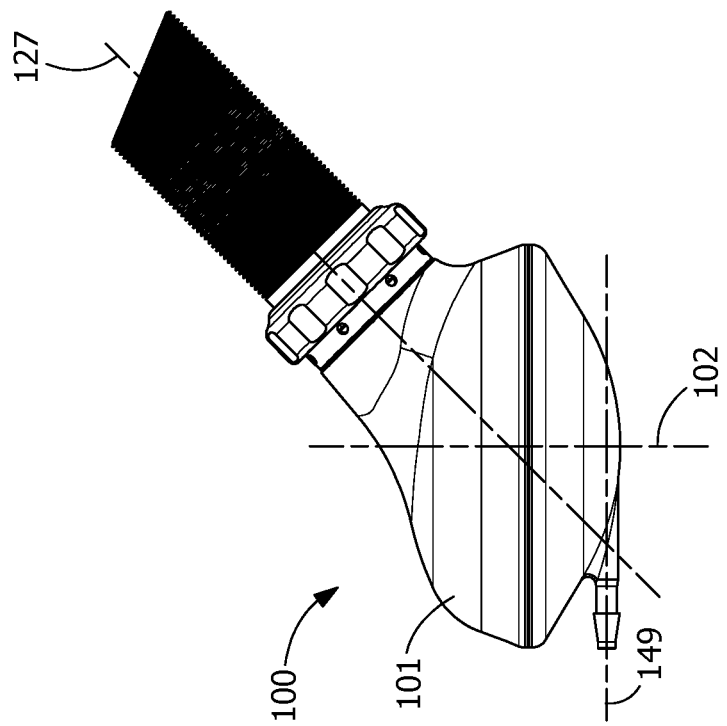
FIG. 1 is a side view of an implantable pump.

Referring now to the drawings, an implantable pump 100 is shown in FIG. 1. The implantable pump 100 includes a rigid housing 101 with an oblate spheroid shape with a blood port 125 and a gas port 147. The rigid housing 101 defines an inner chamber 160 that is divided by a movable elastomeric membrane 200 into a gas sub-chamber 163 and a blood sub-chamber 162. In use, the pump, when connected with a drive source that provides gas flow into the pump based on signals from the heart, operates by displacement of the elastomeric membrane 200 to alternately fill with blood and expel blood back into the body of the clinical subject in synchrony with the flow of gas into and out of the gas sub-chamber 163. In the various embodiments, the inner chamber 160 has a volume that is in a range from about 15 cc to about 100 cc, or from about 40 cc to about 90 cc, or from about 50 cc to about 80 cc, or from about 60 cc to about 70 cc. The volume of the inner chamber 160 is configured to satisfy the anatomical requirements of a recipient of the implantable pump 100. As such, it is contemplated that the implantable pump 100 may be provided in a range of sizes that have inner chamber 160 volumes in a variety of possible ranges. The volume of the inner chamber 160 is configured to properly satisfy the stroke volume supplied by the drive unit (i.e., the volume of fluid that will be displaced from the blood sub-chamber 162 as a result of the inflow of gas into the gas sub-chamber 163). For example, for a 50 cc stroke volume supplied by a driver, the inner chamber 160 may be sized 40% larger (70 cc total volume) to minimize the potential of elastomeric membrane 200 contact with an interior wall of the blood port portion of the rigid housing 101 at full elastomeric membrane 200 inflation. Alternatively, if the stroke volume provided by the driver needs to be decreased to slowly wean a patient off of support, the inner chamber 160 can be sized to facilitate sufficient blood exchange and minimize blood stasis and the potential for blood thrombosis. For example, an inner chamber 160 with 70 cc total volume running at a stroke volume of 35 cc would exchange 50% of blood every stroke and still allow for proper washing of the walls of the blood sub-chamber 162 to minimize stasis.

The gas sub-chamber 163 is connectable to the gas port 147 through a drive line 600 to an external pneumatic source, for example, an intra-aortic balloon implantable pump driver (IABP driver). The blood sub-chamber 162 is connectable via the blood port 125 through a graft assembly 400, that includes, for example, a flexible Dacron® graft, to an anatomical heart. In some examples, one or both of the blood port 125 and the gas port 147 includes an opening that is valveless. For example, as shown in the embodiment represented in the drawings, each of the blood port 125 and the gas port 147 has an opening that is valveless. Advantageously, the absence of valves according to the depicted embodiment eliminate the potential of a point of failure presented by a valve and reduce the potential of thrombus formation].

Figure 4:
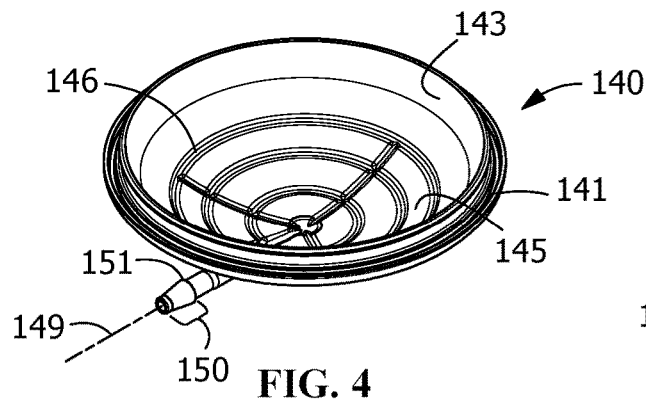
FIG. 4 is a view of a section of the housing of an implantable pump.
Figure 7:
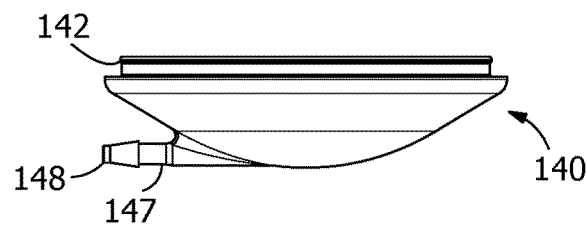
FIG. 7 is a view of a section of the housing of an implantable pump.
Figure 5:
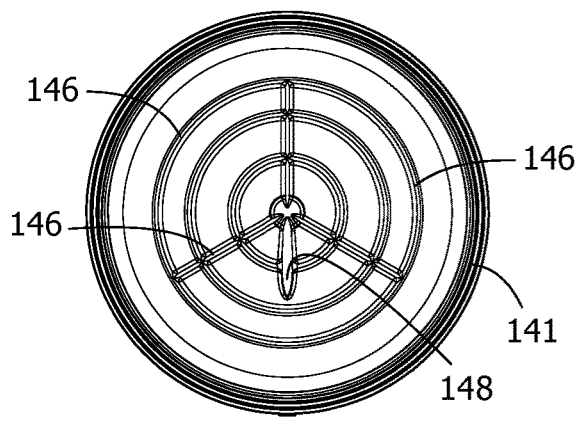
FIG. 5 is a view of a section of the housing of an implantable pump.
Figure 8:
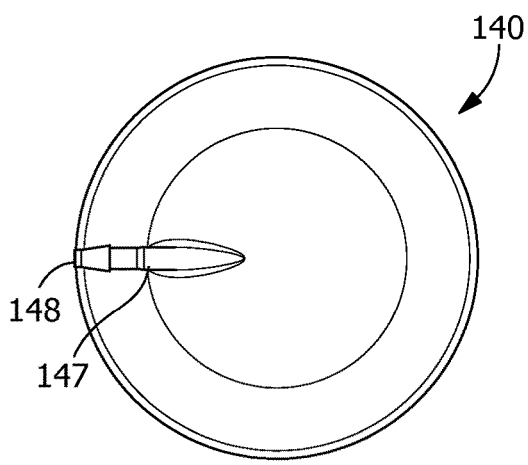
FIG. 8 is a view of a section of the housing of an implantable pump.
Figure 6:
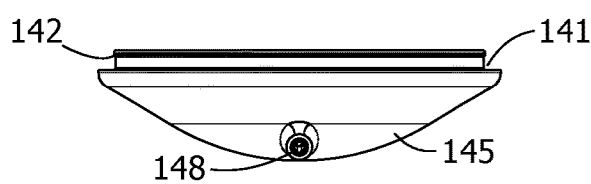
FIG. 6 is a view of a section of the housing of an implantable pump.
Figure 15:
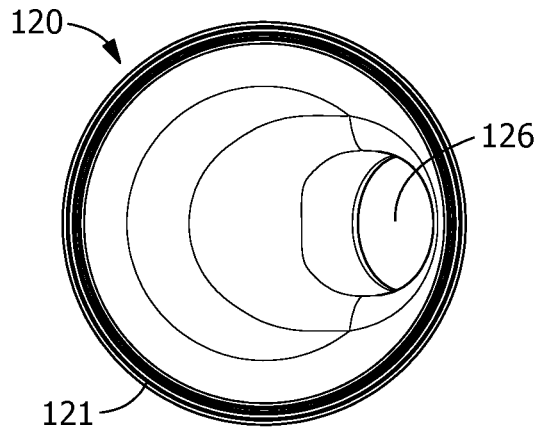
FIG. 15 is a view of a second section of the housing of an implantable pump.
Figure 13:
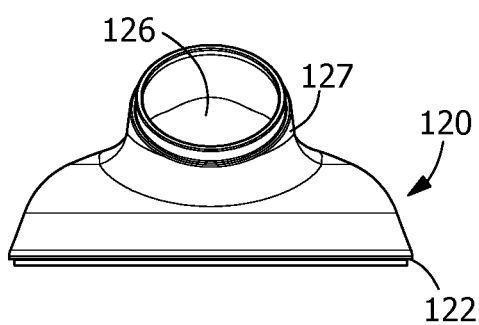
FIG. 13 is a view of a second section of the housing of an implantable pump.

Referring again to the drawings, according to the depicted embodiment of the implantable pump 100, the rigid housing 101 is formed in two parts. Referring now to FIG. 2, the rigid housing 101 is formed in two parts that include a blood port 125 section 120 and a gas port 147 section 140. Each of the blood port 125 section 120 and the gas port section 140, respectively, are depicted in FIG. 4-FIG. 8, and FIG. 11-FIG. 15. As shown, the blood port 125 section 120 and gas port section 140 each forms approximately one half of the rigid housing 101 and are joined at an engagement fitting 121, 141 interface between them, wherein the engagement is located at what is approximately at or below the centerline of the oblate spheroid in a plane that is normal to the central axis 102 of the rigid housing 101. As shown in FIG. 5 and FIG. 15, each of the blood port section 120 and gas port section 140 has a cross sectional shape that is circular, wherein the two sections do not have identical overall shapes. The gas port section 140 is configured to allow for a greater total volume than the blood port section 120, and thus has a shape and overall dimensions that are different from those of the gas port section 140. Referring again to FIG. 2, the distance from the centerplane of the oblate spheroid to the dome of the gas port section 140 (i.e., to the lower apex of the oblate spheroid) is greater than the distance to the dome of the blood port section 120 (i.e., to the upper apex of the oblate spheroid). Also, the curvature of radius for the blood port section 120 is greater than the curvature of the radius of the gas port section 140.

Of course, it will be appreciated that in other embodiments, the rigid housing 101 may be split in another manner, for example along the central axis 102, or may be split in some other manner. Further, it will be appreciated that in some embodiments, the rigid housing 101 is unitary, or may be formed of more than two parts. As depicted the fitting interface between the blood port 125 section 120 and the gas port section 140 includes a snap fitting engagement, each of the engagement fittings 121, 141 having complimentary shapes that each includes a snap fitting tooth 122, 142 and a recess suitable for holding a bead of sealant, such as glue. Of course, in other embodiments, the engagement fittings 121, 141 may engage by a means other than snap fitting, and may, in one example, include complimentary threads or other engagement features known generally in the arts for joining two parts that have a generally circular cross section.

Referring again to the drawings, in accordance with the various embodiments, the rigid housing 101 includes a blood port 125 opening to the blood sub-chamber 162 which is adjacent an upper apex of the rigid housing 101 and has a blood port axis 127 is oriented at an angle relative to the central axis 102 of the rigid housing 101. In various embodiments, the angle is in a range from about zero degrees (i.e., perpendicular/normal relative to the central axis 102) to about 50 degrees, or from about 20 degrees to about 50 degrees, or from about 35 degrees to about 45 degrees. In some specific embodiments, as shown in the represented embodiment shown in the drawings, the angle is about 45 degrees. Of course, the angle may be any angle from and including 20 degrees, 25 degrees, 30 degrees, 35 degrees, 40 degrees, 45 degrees, and 50 degrees, including any subrange and any increment one degree to five degrees therebetween. Thus, in some embodiments, the blood port is oriented at an angle that is in a range from about 20 degrees to about 50 degrees relative to a through axis of the oblate spheroid. In some other embodiments, the blood port is oriented at an angle that is about 0 degrees, or that is in a range from about 1 degree to about 20 degrees relative to a through axis of the oblate spheroid.

Referring again to the drawings, in accordance with the various embodiments, the rigid housing 101 includes a gas port 147 opening to the gas sub-chamber 163, which in the instant depicted embodiment, is the inner chamber 160 outside the sack shaped elastomeric membrane 200. In accordance with the various embodiments, the gas port 147 is situated at a lower apex of the rigid housing 101. As depicted, the gas port 147 is oriented normal to the central axis 102 of the oblate spheroid. It will be appreciated that in alternate embodiments, the gas port 147 may be angled downward at an angle that is in the range from about 1 degree to about 60 degrees relative to the central axis 102 of the rigid housing 101. In the depicted embodiment, the gas port 147 comprises a receiver 150 for attaching a hose to thereby connect the pump to a drive line 600 which in turn is connected to a drive system for the delivery of gas to the pump. The receiver 150 is in the form of a frustoconical hose barb 151 that includes a taper at the exit end of the gas port 147 having a wide base with a diameter that is greater than the outer diameter of the gas port 147 exiting the base 145 of the rigid housing 101. Of course, other forms of engagement may be employed other than a hose barb 151.

In the various embodiments, the gas port 147 defines a gas flow conduit 148 that is generally cylindrical. In some non-limiting examples, for example according to the embodiment of the implantable pump 100 described in the Examples to this disclosure, the gas port 147 may have an inner diameter in the range from about 1 mm to about 5 mm, and is in some embodiments from about 1.5 mm to about 2.0 mm. In some specific examples, the gas port 147 has an inner diameter of less than 2 mm, for example about 1.8 mm.

It will be appreciated that these dimensions are merely representative of an embodiment made and tested according to this disclosure, and other possible dimensions may be employed. Advantageously, the inventors have found benefits that can be obtained when employing gas flow path features that facilitate reducing the inflation air pressure within the inner chamber 160 (i.e., the gas sub-inner chamber 160 163) to a pressure that is just above the native blood pressure of the clinical subject benefitting from the implantable pump 100 (i.e., a relatively small pressure differential exists between the blood side and air side of the elastomeric membrane 200). As described further herein, a system including the implantable pump 100 and a drive line 600 includes additional features that enable delivery of gas in an efficient manner to achieve a controlled pressure differential within the pump.

Figure 3:
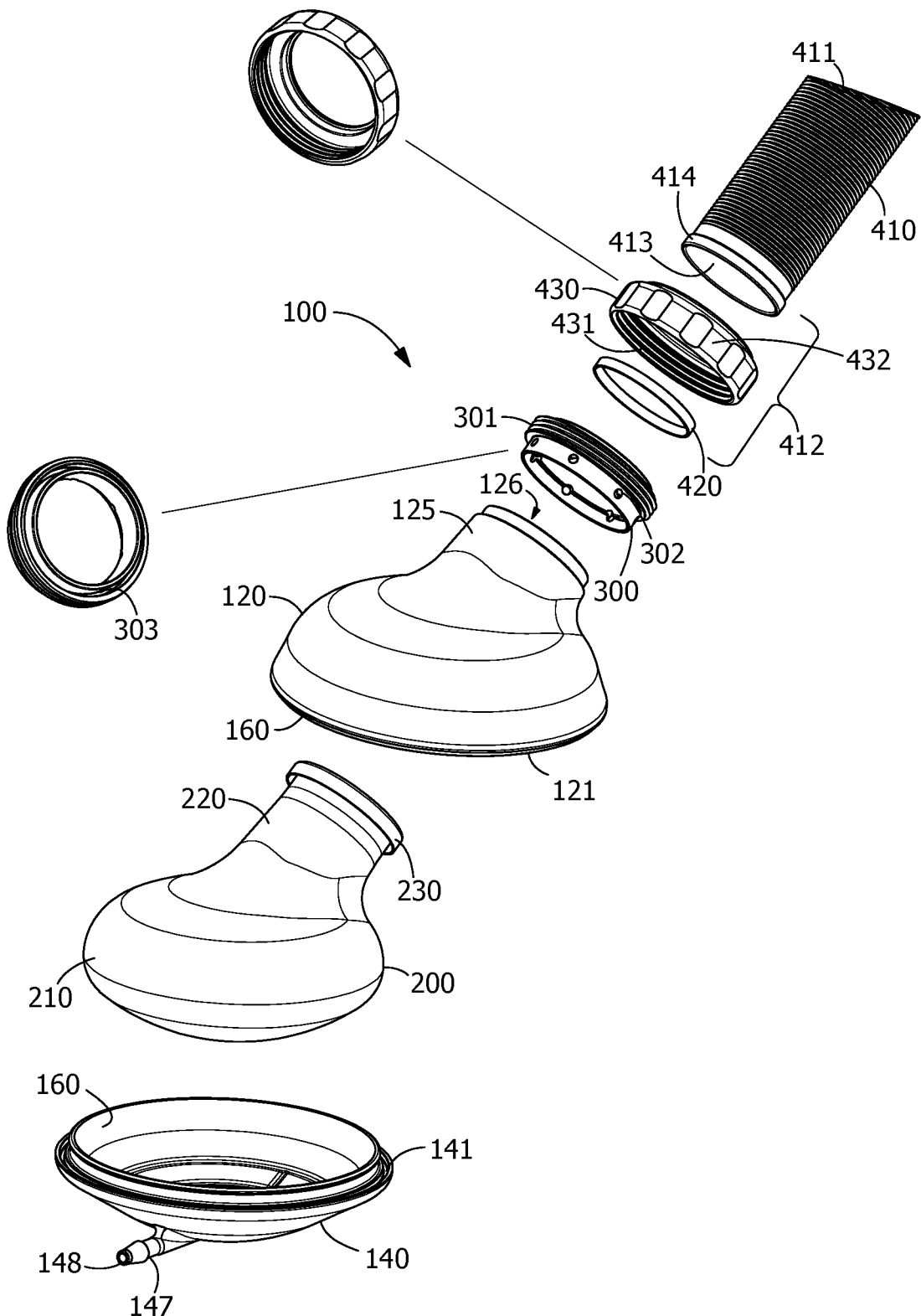
FIG. 3 is an exploded perspective view of an implantable pump.
Figure 9:
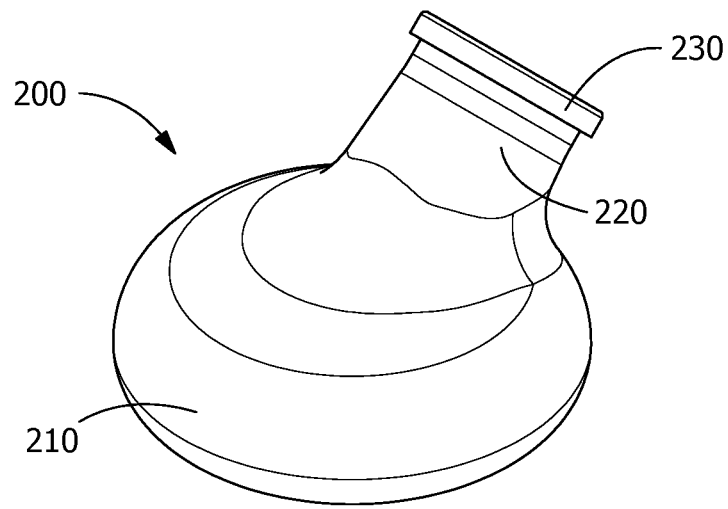
FIG. 9 is a view of a component of an implantable pump.
Figure 10:
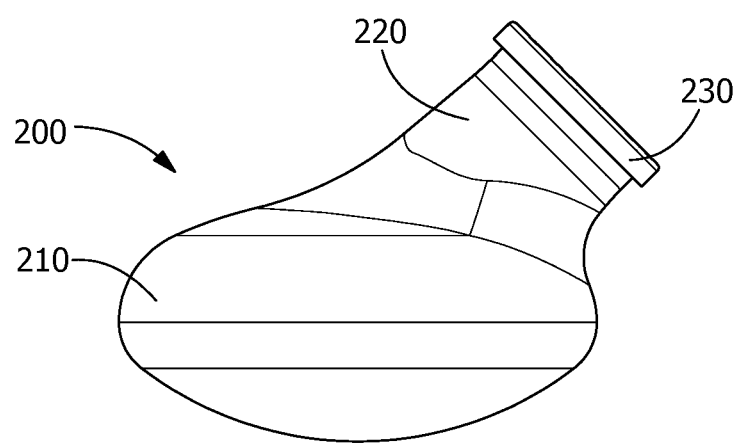
FIG. 10 is a view of a component of an implantable pump.
Figure 11:
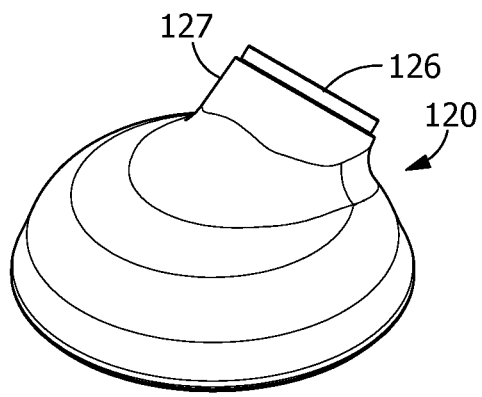
FIG. 11 is a view of a second section of the housing of an implantable pump.
Figure 14:
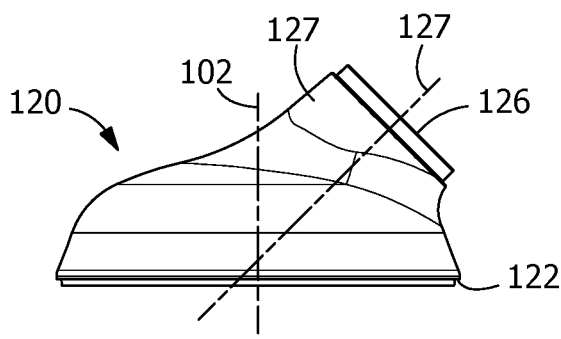
FIG. 14 is a view of a second section of the housing of an implantable pump.
Figure 12:
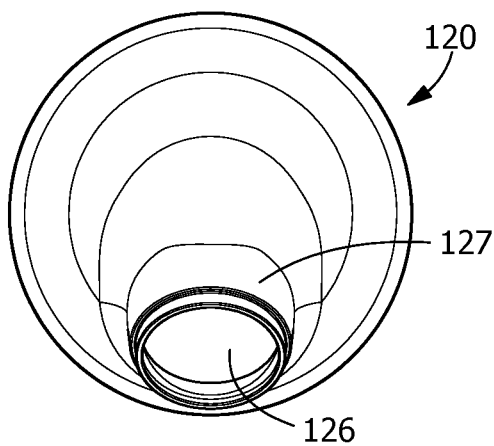
FIG. 12 is a view of a second section of the housing of an implantable pump.

Referring again to the drawings, in accordance with the various embodiments, the implantable pump 100 also includes an elastomeric membrane 200, shown, for example in FIG. 3, and in FIG. 9 and FIG. 10. The elastomeric membrane 200 of the depicted embodiment of the implantable pump 100 defines the blood sub-chamber 162. In some embodiments, the elastomeric membrane 200 has a shape that generally conforms to the inner chamber 160 and the blood port 125 and has an expansion volume that is less than a total volume of the inner chamber 160 and the blood port 125. Of course, in other embodiments, the elastomeric membrane 200 may be a sheet that is affixed within the inner chamber 160, for example secured between edges of discrete sections of the rigid housing 101, or otherwise affixed to an interior structure on a wall of the rigid housing 101 (not shown). Referring again to the drawings, as shown in FIG. 3 and FIG. 9 and FIG. 10, the elastomeric membrane 200 is generally sack shaped. As shown the elastomeric membrane 200 comprises a bulb 210 section, a cylindrical neck 220, and a cuff 230 that interfaces with a rigid housing 101 connector. As depicted, the elastomeric membrane 200 is shaped and adapted to fit within the inner chamber 160 and affixes to the blood port 125 by means of attachment, for example via the rigid housing 101 connector. As shown in FIG. 2 and FIG. 3, in some examples, the elastomeric membrane 200 includes a cuff 230 and is secured to the rigid housing 101 connector.

In accordance with the depicted embodiment, the elastomeric membrane 200 has an expansion volume that is less than 100% of the total volume of the inner chamber 160 and the blood port 125 through channel 126. In some specific examples, the maximum expansion volume of the blood sub-chamber 162, as defined by the elastomeric membrane 200, permits a dead volume 161 of at least about 3 cc to about 20 cc within the inner chamber 160. The dead volume 161 may be slightly greater, for example up to about 25 cc. The elastomeric membrane 200 is formed from any material suitable for contact with blood, for example, medical grade polyurethane. Other examples of suitable materials may include injection molded liquid silicone rubbers and thermoplastic elastomers]. Referring now to FIG. 4 and FIG. 5, the rigid housing 101 includes within the inner chamber 160 on an interior surface 143 one or more shaped features in the form of grooves 146 that serve to ensure a minimum void space that is not occupied by the elastomeric membrane 200 when it is maximally expanded. As shown in the drawings, the grooves 146 include a series of circumferential rings joined by radial lined grooves 146 within the base 145 on the internal surface of the inner chamber 160, the grooves 146 interconnecting to the gas flow conduit 148 that connects to the gas port 147. By this design, the grooves 146 are fluidly connected to the gas flow path such that inflowing and outflowing gas cannot be occluded by the elastomeric membrane 200 at any time during the inflation or deflation cycle (REVIEW). Advantageously, the grooves 146 further ensure that a vacuum is not created should the elastomeric membrane 200 contact the interior surface 143 at the base 145 of the inner chamber 160. It will be appreciated that more or fewer grooves may be employed, and the grooves 146 may have other shapes and forms and dimensions suitable for providing a dedicated space that is resistant to contact with the elastomeric membrane 200. It will also be appreciated that structures other than grooves may be employed, so long as the structures communicate with the gas flow conduit 148 to ensure that the elastomeric membrane 200 cannot collapse and occlude the travel of outflowing gas through the gas port 147.

In accordance with the embodiment depicted in the drawings, the elastomeric membrane 200 is configured smaller than the shape of the gas port section 140, resulting in a void space or dead volume 161 within the base 145 at full elastomeric membrane 200 deflation. As the membrane is inflated, the space between the interior walls of the gas port section 140 and the elastomeric membrane 200 allows for radial movement and expansion of the elastomeric membrane 200, minimizing the formation of buckling in the elastomeric membrane 200 as it fully inflates. This serves to minimize stress on the elastomeric membrane 200 and the potential of fatigue failure. In accordance with some embodiments, the elastomeric membrane 200 may over at least a portion of its outer surface be bonded to an interior wall of the blood port section 120 of the rigid housing 101, the bonding achieved by a medically suitable sealant. The bonding can serve to further secure the elastomeric membrane 200 within the inner chamber 160 to minimize buckling and concentrate flexion of the elastomeric membrane 200 to its lower surface that directly opposes the base 145 of the gas sub-chamber 163.

Referring again to the drawings, the implantable pump 100 further includes a rigid housing 101 connector and a graft assembly 400 as shown in FIG. 3. As shown, the housing connector 300 is employed to secure the elastomeric membrane 200 at its cuff 230 to the blood port 125 of the rigid housing 101. The housing connector 300 includes a generally ring shape engagable with the cylindrical blood port 125, and includes in some embodiments, fenestrations 302. The housing connector may be epoxied to the blood port. Radially located around the housing connector, the fenestrations 302 provide a mechanical interlock and increase surface area to facilitate a stronger bond.] that facilitate securement of the housing connector 300 with the blood port 125. The depicted embodiment of the housing connector 300 also includes a circumferential groove 303 that receives the cuff 230 of the elastomeric membrane 200 for securement at the terminus of the blood port 125. In some other embodiments, engagement between the elastomeric membrane 200 and the housing connector 300 may be by another means. Further, in some embodiments wherein the elastomeric membrane 200 is not in the form of a sack, the housing connector 300 may not have any contact with the elastomeric membrane 200. Referring again to the drawings, as depicted for example in FIG. 3, the housing connector 300 also includes external threading 301 suitable for mating with corresponding threading 431 within the graft connector 430, described below. Of course, it will be appreciated that engagement between the housing connector 300 and graft connector 430 may be other than threaded, and in some alternate examples, the two components may be engagable by other means know in the art, for example employing snap fit, or twist connections.

Referring again to the drawings, the implantable pump 100 further includes a graft assembly 400. In some specific examples, the graft assembly 400 has a tissue attachment end 411, a pump attachment end 412, and comprises a graft conduit 410, a washer 420, and a graft connector 430. As shown, the graft connector 430 is a nut that has interior threading 431 that is complimentary to threading 301 on the rigid housing 101 connector. In some examples, the graft connector 430 and housing connector 300 may have alternate configurations, wherein the housing connector 300 includes internal threading and the graft connector 430 includes external threading for engagement therebetween. And, of course, as mentioned herein with respect to the housing connector 300, the two connectors may engage by means other than complimentary threading. The depicted graft assembly 400 also includes a washer 420. Referring now to FIG. 2, the washer 420 is integrated into the pump attachment end 412 of the graft conduit 410 to provide hoop strength that prevents collapse of the graft conduit 410 and facilitates its securement within the graft connector 430. In some examples, the graft material of the graft conduit 410 is first stretched and folded onto the washer 420 and secured with thin suture stitches where the two layers of graft material overlap.

Referring again to the drawings, the graft assembly 400 further includes a graft conduit 410 having a generally cylindrical shape that is flexible and suitable for surgical attachment to biological tissue, for example the aorta of a heart. The graft conduit 410 is provided suitable for trimming at its tissue attachment end 411 to achieve a length and specific angulation selected by the surgeon for attachment to the aorta. The graft conduit 410 may be formed of any suitable material for contact with blood based biological materials, for example, one or more of gelatin sealed, woven polyester grafts, and flexible Dacron® material. When engaged with the housing connector 300, the graft assembly 400 provides a continuous blood flow path 500 defined by the lumen of the conduit 410 and the through channel 126 of the blood port 125. In the depicted embodiment, each of the blood port 125 and graft conduit 410 having an internal surface, each such internal surface having essentially the same diameter at an internal surface interface 501 therebetween, such that the internal surface interface 501 between the engaged blood port 125-housing connector 300-graft assembly 400 provides for zero stepdown such that the continuous blood flow path 500 has a uniform diameter.

Figure 16:
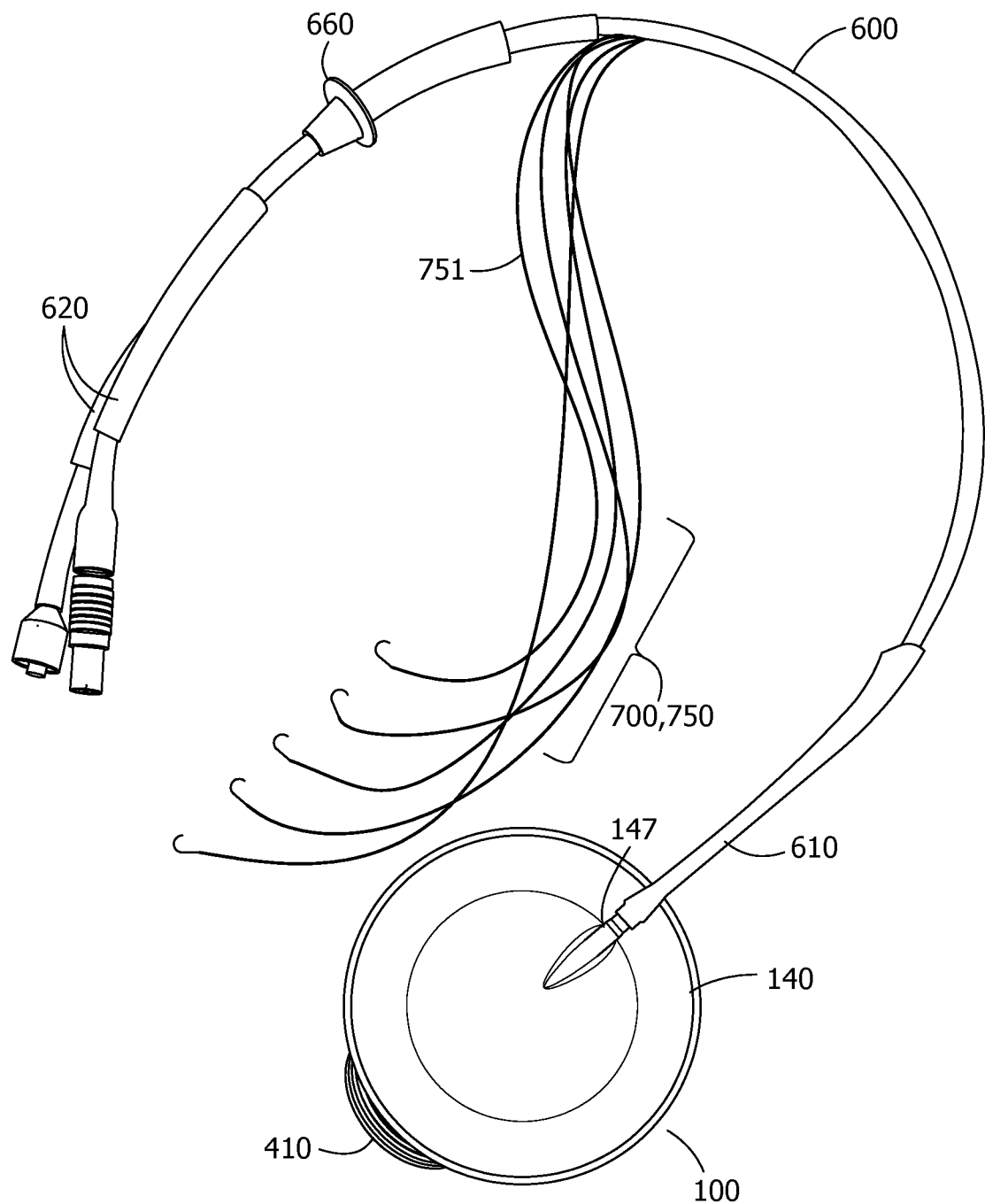
FIG. 16 is a schematic of a system that includes an implantable pump and a drive line.

Referring again to the drawings, in accordance with the various embodiments also provided is a novel drive line 600 attachable to the implantable pump 100 to form a blood pump system. The drive line 600 provides the interface between the pump and a drive system which is configured to provide gas flow into the pump based upon heart function signals obtained through sensors implanted in the clinical subject. FIG. 16 shows a representative example of an embodiment of the pump connected to an embodiment of a drivel line 600. As depicted, the drive line 600 includes along at least a portion of its length a linear integration of a gas conduit 630 and a sensor conduit 640, the drive line 600 having a first end that includes respective first ends of the gas conduit 630 in communication with the implantable pump 100 and of the sensor for connection to the patient, and a second end for attachment to the driver.

In some examples, the gas conduit 630 portion of the drive line 600 includes a disc shaped circumferential flange 660 that is adapted for positioning below the skin or dermis at the driveline exit site of a clinical subject into whom the implantable pump 100 has been implanted. The circumferential flange 660 is designed to provide a compliant transition of the drive line 600 and reduce exit site trauma and infection, and may be made of any suitable material, including for example medical grade silicone. The drive line 600 may further include an intermediate connection hub whereby the second ends of the gas conduit 630 and sensor conduit 640 may be disconnected from the patient contact ends. And the drive line 600 may include an integrated patient safety circuit for limiting any damaging current that may pass into the patient.

Figure 19:
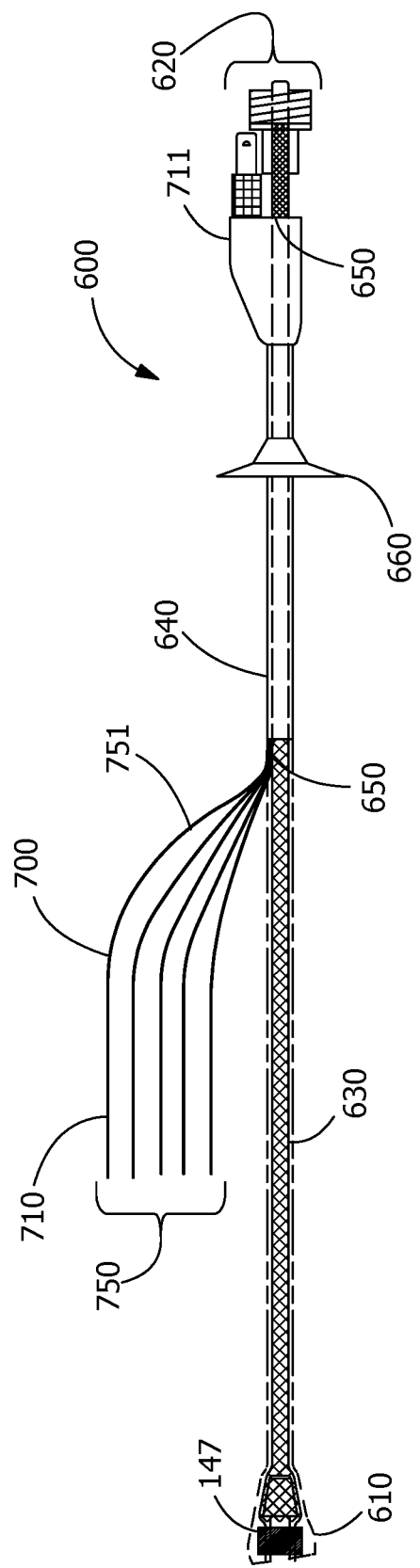
FIG. 19 is a schematic of a drive line.

Referring now to FIG. 19, the drive line 600 includes a pair of conduits comprising a gas conduit 630 and a sensor conduit 640 that are contiguously connected over at least a portion of a length of the drive line 600 and are split apart at a drive line split 650 each of a first end 610 and a second end 620 of the drive line 600, the drive line 600 further comprising a circumferential disc shaped flange 660 positioned between the first end 610 and the second end 620 prior to a drive line split 650 between the pair of conduits. Referring now to FIG. 16, the first end 610 of the gas conduit 630 is attachable to a gas port 147 of an implantable pump 100, and the first end 710 of the sensor conduit 640 is attachable to an anatomical site of a clinical subject. Each of the gas conduit 630 attachable at the second end 620 to a drive system, wherein the gas and sensor connections at the second end 620 are connected in turn an external cable and air line that is connectible to the drive system.

Referring again to the drawings, the gas conduit 630 includes an internal gas flow channel that may be integrally formed in the conduit or may include a tube within the conduit. The flow channel communicates through a connection with the gas port 147 of an implantable pump 100 to deliver gas inflow and outflow and includes at each of its first and second ends attachment features suitable for stable connection to each of the implantable pump 100 and the driver. In various embodiments, the gas flow channel has an inner diameter in the range from about 1 mm to about 4 mm, and via attachment features at its first end. The gas conduit 630 is attachable to the implantable pump 100 at the gas port 147 in a manner that enables air flow restriction going into the pump in order to control the inflation air pressure within the pump to just above the blood pressure. Thus, the gas conduit 630 is adapted to enable a step down in flow channel diameter from the conduit's flow channel to the pump's gas port 147.

In some alternate embodiments, the gas conduit 630 may be provided in more than one part along the length of the drive line 600, and may, for example be provided as a "two-piece" embodiment where a length of the gas conduit 630 includes a separate tube, for example one that has a diameter that is smaller than a diameter close to the second, drive attachment end 620 of the gas conduit 630. Employment of a coupler, such as a double barb connector at ends of the second tube may facilitate replacement of the tubing for new tubing having the same, or a different internal diameter. Of course, it will be appreciated that a step down design is but one option for gas flow control between the driver, the drive line 600 and the implantable pump 100, and in other embodiments, there may be more or fewer step down features, and in some embodiments, the flow channel as well as the gas flow conduit 148 may have the same diameter. According to the various embodiments, the drive line 600 includes a gas conduit 630 that may include one or a series of tubes such that the inner diameter along the length of the drive line 600 may be continuous with the inner diameter of the gas port 147 (e.g., 1 mm-5 mm, or 1.8 mm), or may in some embodiments include a step up to a greater diameter (e.g., greater than 2 mm) as the gas conduit 630 is closer to the second end 620 of the drive line 600.

Figure 18:
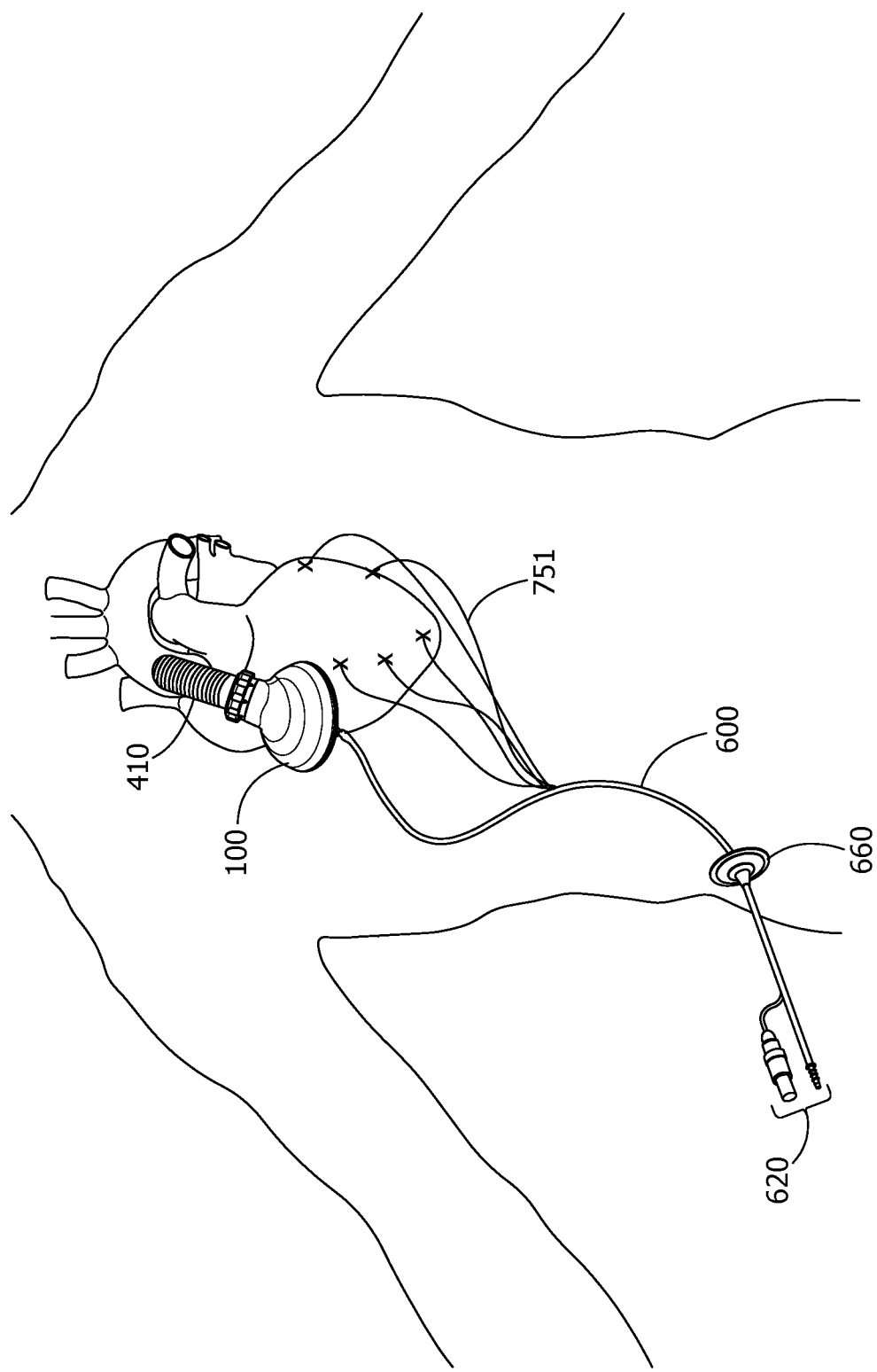
FIG. 18 is a schematic of a system that includes an implantable pump and a drive line in the context of human anatomy.

Referring again to the drawings in FIG. 19, the sensor conduit 640 includes a heart sensor 700 for monitoring heart rhythm of the clinical subject. In the various embodiments, the heart sensor 700 is selected from one or more of a plurality of electrodes, and fiber optic sensors. As depicted in FIG. 16 and FIG. 18, the heart sensor 700 is a plurality of electrodes, and as specifically shown the plurality includes five electrodes 751.

In some alternate embodiments, the sensor 700 may include fewer or more electrodes, and these may be selected for placement on portions of the clinical subject's anatomy other than the pericardium. In some embodiments, the sensor 700 may include one or more pressure type sensors or other sensors suitable for detecting heart function other than electrically, and these may be placed within the lumen of one or more anatomical vessels. According to the exemplified embodiment, the use of electrodes, specifically myocardial electrodes, provides good results with the implantable pump 100 because this allows interface with a wide range of conventional IABP drive units since most (if not all) require five skin ECG leads. It is well known in the art that conventional IABP drive units employ five ECG leads to time the inflation/deflation of the balloon that is implanted in the patient's vasculature. For use with the instant implantable pump 100, the employment of five electrodes 751 that are affixed to the pericardium of the subject's heart avoids the need for a custom driver for the pump. And commercially available IABP units have pacing algorithms that sense the five skin leads and automatically select the best signal from among the leads, thus avoiding the need to rely on development of a new driver system. These units can also trigger inflation/deflation based on aortic pressure, sensed for example using a fiber optic sensor, thus supporting alternate embodiments of the drive line 600 that employ one or more fiber optic sensors placed within a lumen of the clinical subject. The disclosure is not limiting in the sense that a variety of possible heart sensors may be selected and employed for use with any of a variety of known and possible custom drivers that provide the functionality of gas flow responsive to signals from the clinical subject.

Surgical Technique

Figure 17:
FIG. 17 is a schematic of a heart.

In accordance with the disclosure and in the various embodiments, a surgical technique is provided for promoting blood flow to support a diseased and/or damaged heart. In some examples, the clinical subject is a human patient. According to the technique, the clinical subject is first prepared for receiving an implantable pump 100, whereby access to the thoracic cavity is achieved to enable placement of a blood implantable pump 100 in fluid communication with the patient's ascending aorta. Referring to the drawings, FIG. 17 is a schematic that shows possible placement position of electrodes on the pericardium of a heart, and FIG. 18 is a schematic that shows the implantable pump 100 attached to the aorta of a human subject and connected drive line 600 attached to the pump and passing through the subject's skin at the flange.

An implantable pump 100 is provided according to an embodiment disclosed herein. In an example, an implantable pump 100 is provided that has a rigid housing 101 with an oblate spheroid shape and having an inner chamber 160, the rigid housing 101 including a blood port 125 opening to the inner chamber 160, the blood port 125 adjacent an upper apex of the oblate spheroid and oriented at an angle that is from about 0 degrees to about 50 degrees relative to a central axis 102 of the oblate spheroid, and a gas port 147 opening to the inner chamber 160, the gas port 147 situated at a lower apex of the oblate spheroid and having a gas port axis 149 oriented normal to the central axis 102 of the oblate spheroid, the implantable pump 100 including an internal elastomeric membrane 200 that generally conforms to the inner chamber 160 and the blood port 125, and has an expansion volume that is less than a total volume of the inner chamber 160 and the blood port 125. In an initial placement step, the implantable pump 100 is positioned between the heart and the right lung of the clinical subject, followed by at least partial clamping the ascending aorta of the clinical subject.

A graft assembly 400 is provided that includes a flexible graft conduit that includes a tissue attachment end 411 and an implantable pump attachment end 412 that includes a washer 420, and a graft connector 430. The tissue attachment end 411 of the flexible graft conduit is anastomosed to the partially clamped aorta and is ready for attachment to the implantable pump 100.

A drive line 600 is provided, the drive line 600 including a gas conduit 630 attachable at a first end to the gas port 147 of the implantable pump 100, a sensor conduit 640 and a heart sensor passed therethrough, the heart sensor comprising one or more of a plurality of electrodes and fiber optic sensors. The drive line 600 includes a flexible flange at a point along its length. The drive line 600 is then passed through an incision in the clinical subject with the flange abutting the incision on the outside of the clinical subject's body. A gas conduit 630 of the drive line 600 is then attached to the gas port 147 of the implantable pump 100. Each of the one or more of a plurality of electrodes and fiber optic sensors is positioned on an anatomical structure of the clinical subject selected from a portion of the pericardium, and within one of the pulmonary artery and the arterial artery. In a particular example, the heart sensor includes a plurality of electrodes 750, for example, five electrodes, each of which is affixed to the pericardium of the clinical subject, for example as shown in FIG. 17 and FIG. 18. The electrodes may be myocardial electrodes. Thereafter, the gas conduit 630 and sensor conduit 640 of the drive line 600 are attached to the drive system.

Once the drive components are placed and connected, the implantable pump 100 is affixed to the graft assembly 400 by engagement between the graft connector 430 and a rigid housing 101 connector on the blood port 125 of the implantable pump 100. The blood port 125 of the implantable pump 100 will ideally be oriented within the clinical subject's anatomy at angle to allow for close anatomical fit of the implantable pump 100 between the heart and the right lung and attachment to the ascending aorta without kinking the graft conduit and without superior vena cava compression. The clamp is then removed from the clinical subject's aorta to permit blood flow from the heart into the blood implantable pump 100 via the graft, and the drive system is activated to provide support to the heart.

Ideally, the surgical technique is carried out without employment of heart lung bypass.

EXAMPLES

Example 1: Surgical Procedures and Experimental Protocol

Seven farm pigs weighing 80-90 kg were studied using the disclosed implantable device (referred to herein as "the PULVAD"). All animals underwent median sternotomy and implantation of the PULVAD in the ascending aorta. The device was connected to a conventional IABP driving console with a flexible driving line. Temporary pacemaker leads were implanted in the pericardium for ECG monitoring and the PULVAD was synchronized based on the ECG to provide diastolic aortic pressure augmentation. Animals were instrumented with 1) catheters in the common carotid artery (to record aortic pressure) and the right external jugular vein (to monitor right atrial pressure and administer fluids); 2) a Millar pressure-tip catheter to record LV pressure; 3) four piezoelectric crystals (implanted in the LV subepicardium) to measure LV volumes11; and 4) a Doppler flow probe placed around the left anterior descending (LAD) artery to measure blood flow. Baseline measurements of aortic and LV pressures were obtained. Myocardial ischemia was then induced by ligation of mid-LAD artery for 1 hour, followed by reperfusion. After 15 minutes of hemodynamic stabilization during reperfusion, ventilation was suspended at end-expiration and the following parameters were recorded without PULVAD support: arterial and LV pressures, heart rate, double product (systolic arterial pressure Å~heart rate), distances between piezoelectric crystals (for LV volume calculation), ejection fraction (EF), SV, cardiac output (CO), stroke work (SW) (the area within the pressure—volume loop), dP/dT max, dP/dT min and LAD blood flow. Then the PULVAD was turned on and the aforementioned parameters were recorded once a new hemodynamic steady state was achieved with the PULVAD on. The duration of PULVAD support (until the new hemodynamic steady state was achieved) varied between 30 and 60 seconds. Subsequently, the inferior vena cava was gradually and partially occluded and a family of pressure—volume loops (at decreasing preload) was obtained without PULVAD support and during PULVAD support (after the first 30-60 seconds) to determine the end systolic pressure—volume relationship (ESPVR) and the end diastolic pressure—volume relationship (EDPVR). From the slope of the ESPVR, the load-independent index of contractility maximum elastance (Emax) was calculated. From the ESPVR and the EDPVR, pressure—volume area (PVA) (a proxy for myocardial oxygen consumption calculated as the area contained within the ESPVR, EDVPVR, and the systolic segment of the pressure—volume loop) was measured. The ratio of SW to PVA was calculated as an index of energetic efficiency of LV mechanical performance. The experiment was terminated after successful collection of at least 3 pairs of consecutive recordings (with the PULVAD off and on) by electrical fibrillation of the heart. Data were analyzed with the CardioSoft Pro software (Sonometrics Corporation, London, Canada).

Example 2: Statistical Analysis

Data are presented as mean±standard deviation in the text and tables and as mean±standard error of the mean in the figures. Data obtained from consecutive recordings (without and after 30-60 seconds of PULVAD support, with the PULVAD on) were compared using paired t test. The coefficient r was calculated to examine the presence of correlations between variables by linear regression analysis. All tests were two sided, and a p value<0.05 was considered statistically significant.

Figure 20:
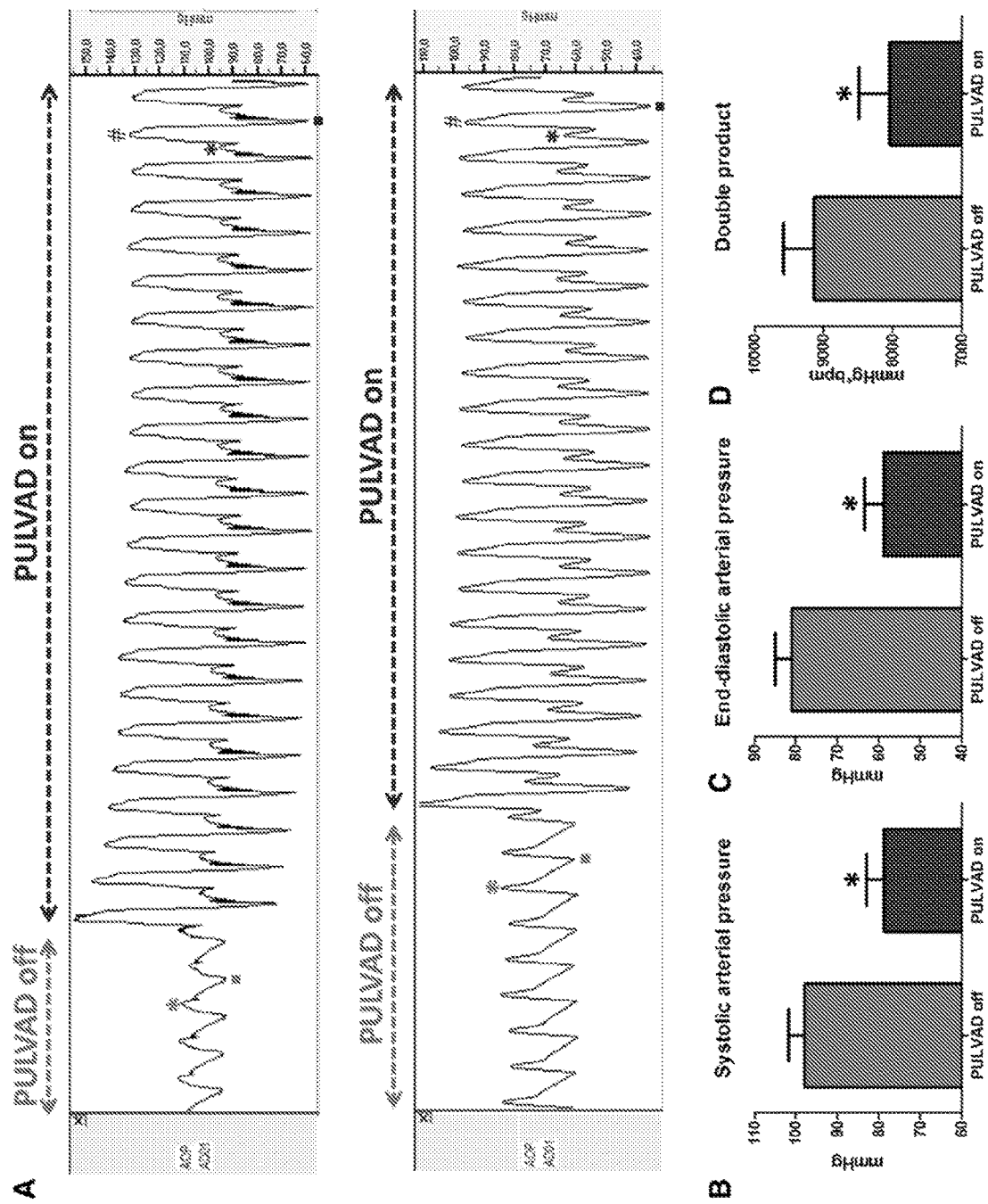
FIG. 20 provides results related to cardiac pressure unloading using the disclosed implantable device.

Example 3: Pressure Unloading Left Ventricular Assist Device Support Provides Marked Left Ventricle Pressure Unloading Referring to the drawings, FIG. 20 shows that the PULVAD provides profound pressure unloading of the failing LV. A: Aortic pressure waveforms without (PULVAD off) and with PULVAD support (PULVAD on). The PULVAD decreased systolic aortic pressure (from 112 to 95 mm Hg [top]; from 85 to 65 mm Hg [bottom]) and end-diastolic pressure (from 85 to 65 mm Hg [top]; from 60 to 35 mm Hg [bottom]). Note that the magnitude of PULVAD-induced afterload reduction is similar over a wide range of systolic aortic pressures. Despite the dramatic decrease in systolic aortic pressure, mean aortic pressure remains normal due to diastolic pressure augmentation provided by the qjPULVAD. *Systolic aortic pressure; ■end-diastolic pressure; #Diastolic pressure augmentation. Quantitative analysis of PULVAD-induced changes in systolic arterial pressure (B), end-diastolic arterial pressure (C), and double product (D) (*p<0.05 compared with PULVAD off). PULVAD, pressure unloading left ventricular assist device.

Left anterior descending ligation resulted in induction of acute HF, manifested as a significant increase in LV end diastolic pressure (baseline: 9.3±1.4 mm Hg, acute HF: 16.4±5.6 mm Hg; p<0.001). Pressure unloading left ventricular assist device support provided profound pressure unloading of the failing LV, manifested as a significant decrease in LV afterload; systolic aortic pressure decreased by 19.2±8.6 mm Hg, end-diastolic aortic pressure decreased by 22.3±10.7 and double product decreased by 1094±921 mm Hg.bpm (FIG. 20, Table 1). Representative aortic pressure waveforms without and with PULVAD counterpulsation are provided in FIG. 20A, demonstrating the dramatic PULVAD-induced decrease in systolic and end-diastolic aortic pressure and increase in diastolic arterial pressure.

Figure 21:
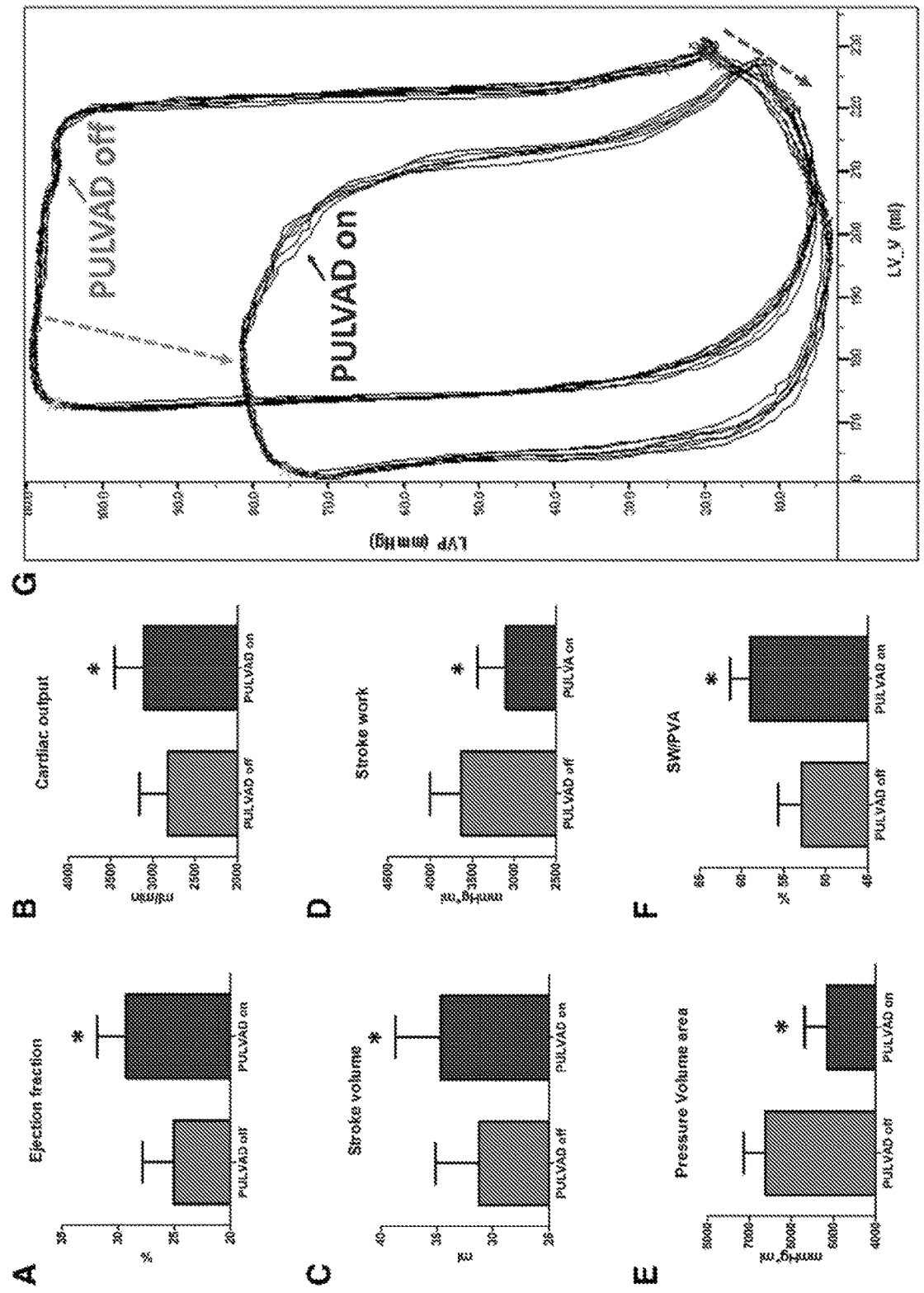
FIG. 21 provides results related to optimization of cardiac mechanoenergetics using the disclosed implantable device.

Example 4: Pressure Unloading Left Ventricular Assist Device Support Optimizes Left Ventricle Mechanoenergetics Referring again to the drawings, FIG. 21 shows that the PULVAD optimizes LV mechanoenergetics (improves mechanical performance and decreases energy consumption) in acute HF. Quantitative analysis of PULVAD-induced changes in EF (A), CO (B), SV (C), SW (D), pressure—volume area (E), and ratio of SW to pressure—volume area (F) (*p<0.05 compared with PULVAD off). G: Representative pressure—volume loops of a failing porcine LV without (PULVAD off) and during brief PULVAD support (PULVAD on). PULVAD support produces a dramatic shift of the pressure—volume loop to the bottom (profound pressure unloading) and to the left (indirect volume unloading). In addition, PULVAD support optimizes LV mechanoenergetics; SV and EF increase, and at the same time, stroke work (measured as the area within the loop) decreases. CO, cardiac output; EF, ejection fraction; HF, heart failure; PULVAD, pressure unloading left ventricular assist device; PVA, pressure—volume area; SV, stroke volume; SW, stroke work.

TABLE 1

Effects of PULVAD Support on Hemodynamics, LV Mechanical Performance, Energy Consumption, and LAD Blood Flow in Acute HF

| Feature | PULVAD Off | PULVAD On | p |
|---|---|---|---|
| Systolic arterial pressure (mm Hg) | 97.9 ± 23.0 | 78.7 ± 24.9 | <0.001 |
| End-diastolic arterial pressure (mm Hg) | 81.0 ± 24.1 | 58.6 ± 28.5 | <0.001 |
| LV end-diastolic pressure (mm Hg) | 16.4 ± 5.6 | 12.4 ± 5.8 | <0.001 |
| Heart rate (bpm) | 92.1 ± 10.0 | 91.6 ± 11.6 | 0.274 |
| Double product (mm Hg · bpm) | 9131 ± 2603 | 8038 ± 2637 | <0.001 |
| Stroke work (mm Hg · ml) | 3633 ± 1693 | 3096 ± 1559 | <0.001 |
| PVA (mm Hg · ml) | 6625 ± 2312 | 5153 ± 2433 | <0.001 |
| Stroke work/PVA (%) | 52.8 ± 12.8 | 59.0 ± 10.7 | 0.003 |
| Ejection fraction (%) | 25.1 ± 14.0 | 29.3 ± 13.0 | <0.001 |
| Stroke volume (ml) | 31.3 ± 19.8 | 34.7 ± 20.4 | <0.001 |
| Cardiac output (L/min) | 2.82 ± 1.7 | 3.11 ± 1.8 | <0.001 |
| End-diastolic volume (ml) | 119.1 ± 54 | 113.3 ± 54 | <0.001 |
| End-systolic volume (ml) | 87.8 ± 43 | 78.6 ± 40 | <0.001 |
| dP/dT max (mm Hg/sec) | 1315 ± 459 | 1110 ± 486 | <0.001 |
| dP/dT min (mm Hg/sec) | −979 ± 249 | −782 ± 298 | <0.001 |
| Emax (mm Hg/ml) | 1.49 ± 0.6 | 2.23 ± 0.8 | 0.034 |
| Mean LAD blood flow (ml/min) | 50.8 ± 23 | 64.6 ± 24 | 0.018 |
| Systolic LAD blood flow (ml/min) | 32.5 ± 14 | 11.0 ± 28 | 0.090 |
| Diastolic LAD blood flow (ml/min) | 62.4 ± 31 | 98.3 ± 36 | 0.001 |

HF, heart failure; LAD, left anterior descending artery; PULVAD, pressure unloading left ventricular assist device; PVA, pressure—volume area.

Pressure unloading left ventricular assist device support improved the mechanical performance of the failing LV, manifested as a significant increase in LVEF, SV, and CO (FIG. 21, A-C, Table 1). The PULVAD-induced enhancement of LV mechanical performance was accompanied by a concurrent decrease in SW and total LV energy consumption (as measured by PVA) (FIGS. 21, D and E, Table 1). In addition, PULVAD support optimized LV mechanoenergetic efficiency, indicated by an increase in the ratio of SW to PVA (FIG. 21F, Table 1). Moreover, PULVAD support produced indirect volume unloading of the LV, as there was a significant decrease in LV EDV (and consequently in LV end-diastolic pressure) (Table 1). This indirect volume unloading of the LV can be rationalized as follows: in the setting of PULVAD-induced improved LV systolic performance, the LV preload (i.e., LV end-diastolic volume) is physiologically adjusted to the lowest necessary levels for the LV to eject a SV adequate to meet peripheral needs, as determined by the Frank-Starling law.

FIG. 21G shows representative pressure—volume loops of a failing porcine LV without and during PULVAD support. Pressure unloading left ventricular assist device support produces a dramatic shift of the pressure—volume loop to the bottom (profound pressure unloading) and to the left (indirect volume unloading). In addition, PULVAD support optimizes LV mechanoenergetics; SV and EF increase, and at the same time, SW (measured as the area within the loop) decreases.

Figure 22:
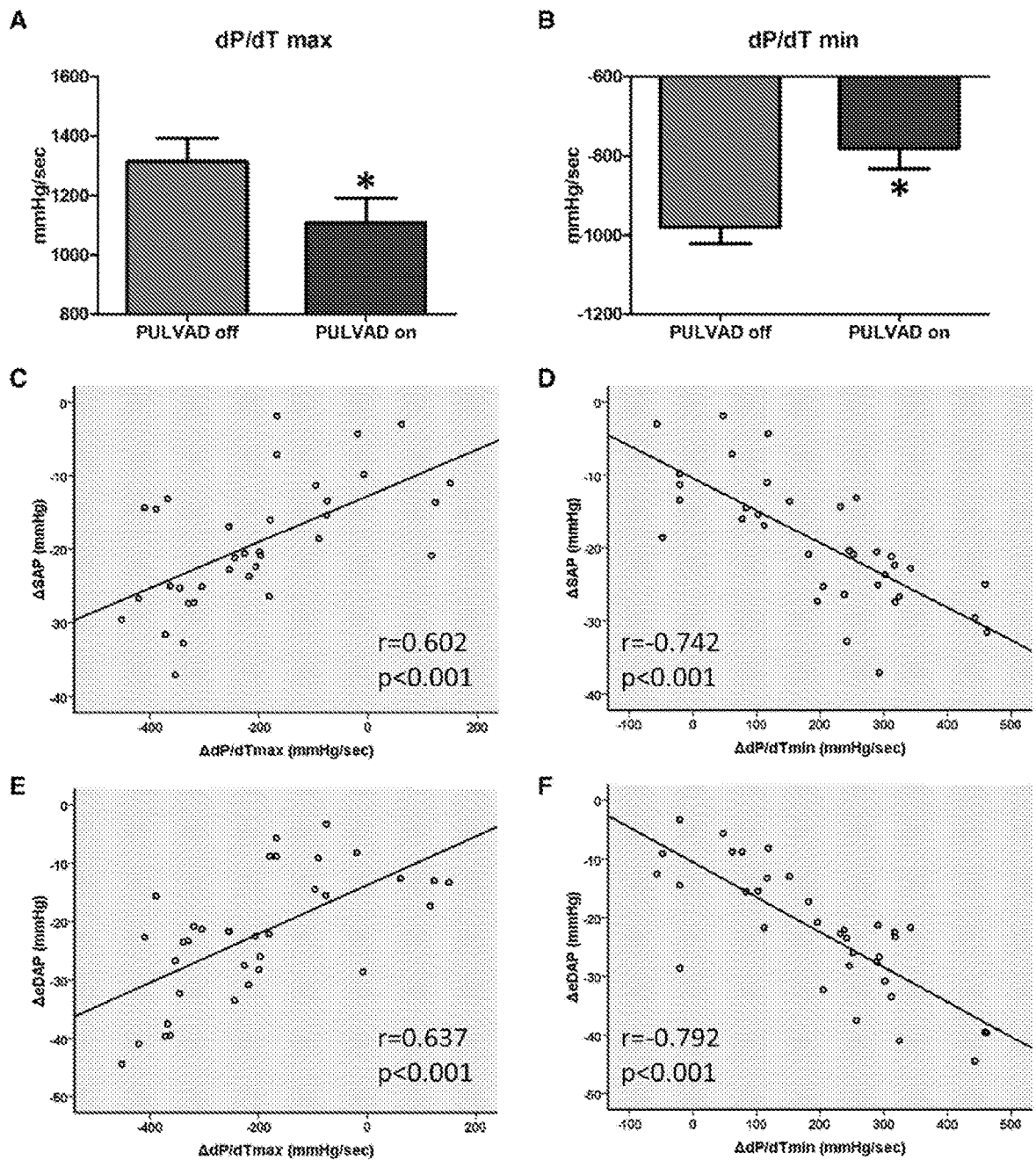
FIG. 22 provides results related to cardiac blood pressure using the disclosed implantable device.

Example 5: Pressure Unloading Left Ventricular Assist Device Support Improves Left Ventricle Contractility Referring again to the drawings, FIG. 22 shows the PULVAD effect on dP/dT max and dP/dT min. Quantitative analysis of PULVAD-induced changes in dP/dT max (A) and dP/dT min (B) (*p<0.05 compared with PULVAD off). C-F: PULVAD-induced changes in dP/dT max and dP/dT min correlated significantly with PULVAD induced decreases in systolic and end-diastolic arterial pressure during ischemia. PULVAD, pressure unloading left ventricular assist device.

In the acute HF setting, PULVAD support induced a significant decrease in dP/dT max and a significant increase in dP/dT min. However, dP/dT max and dP/dT min are load dependent (they improve as afterload increases) and the inventors have previously shown that afterload reduction induced by counterpulsation (using the IABP) correlates significantly with changes in dP/dT. The changes of dP/dT max and dP/dT min during PULVAD support correlated significantly with PULVAD-induced decreases in systolic and end diastolic arterial pressure (used as markers of cardiac afterload) (FIG. 22). Thus, the decrease in dP/dT max and the increase in dP/dT min observed during PULVAD support should be attributed to pressure unloading (i.e., reduction in cardiac afterload), rather than be interpreted as PULVAD-induced deterioration of LV systolic and diastolic function.

Figure 23:
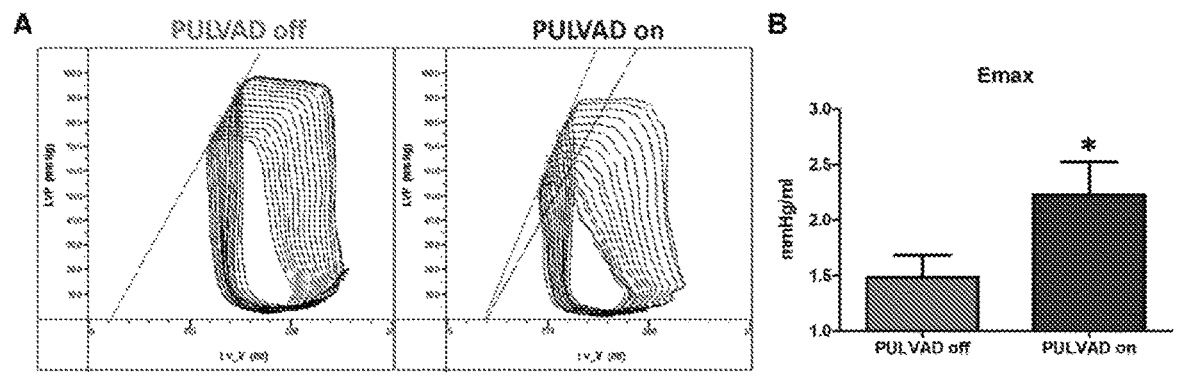
FIG. 23 provides results related to cardiac contractility of the failing LV using the disclosed implantable device.

Referring again to the drawings, FIG. 23 shows that the PULVAD support improves the contractility of the failing LV. A: Families of pressure—volume loops (at decreasing preload) without and after brief PULVAD support. Maximum elastance (Emax, i.e., the slope of the end-systolic pressure—volume relationship) increases after PULVAD support. The dashed line on the right denotes the slope of the solid line on the left (PULVAD off). B: Quantitative analysis of PULVAD induced change in Emax (*p<0.05 compared with PULVAD off). PULVAD, pressure unloading left ventricular assist device. PULVAD support induced a significant increase in Emax, manifested as a steeper slope of the ESPVR (FIG. 23, Table 1), suggesting improved contractility of the failing LV.

Figure 24:
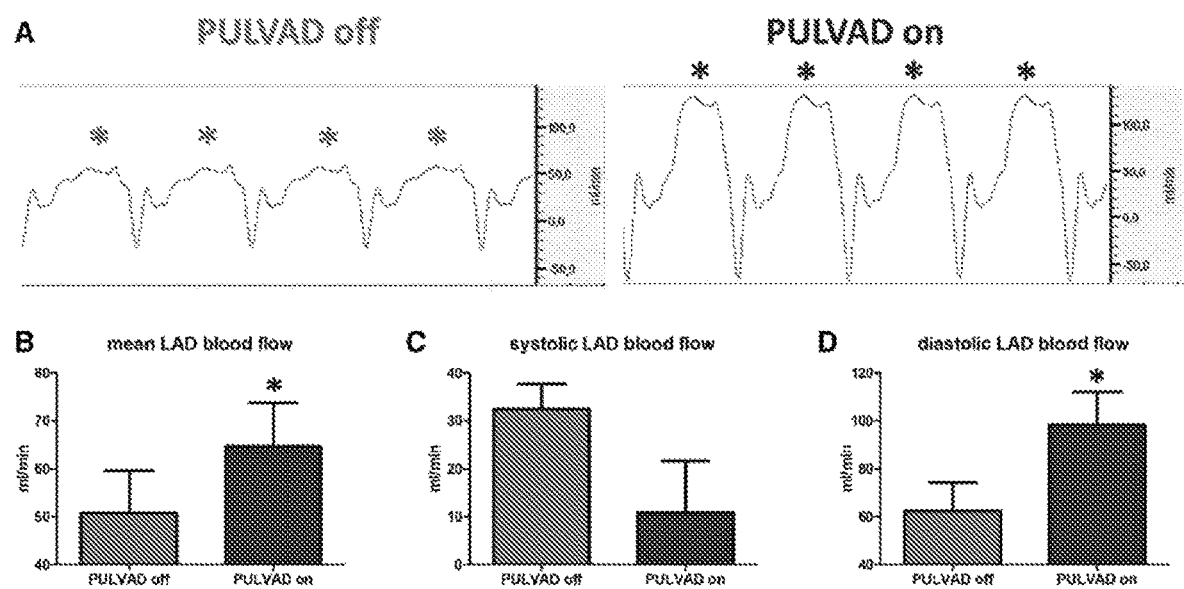
FIG. 24 provides results related to cardiac coronary blood flow in the failing heart using the disclosed implantable device.

Example 6: Pressure Unloading Left Ventricular Assist Device Support Increases Left Anterior Descending Blood Flow in Reperfused Myocardium Referring again to the drawings, FIG. 24 shows that the PULVAD increases coronary blood flow in the failing heart. A: LAD blood flow waveforms without and with brief PULVAD support during reperfusion. Note the dramatic augmentation in diastolic blood flow (denoted by *) induced by PULVAD. Quantitative analysis of PULVAD-induced changes in mean LAD blood flow (B), systolic LAD blood flow (C) and diastolic LAD blood flow (D) (*p<0.05 compared with PULVAD off). LAD left anterior descending artery; PULVAD, pressure unloading left ventricular assist device. FIG. 24A shows representative LAD blood flow recordings without and with PULVAD support in the acute HF setting. While PULVAD support decreased LAD blood flow during systole (from 32.5±13.9 to 11.0±28.0 ml/min; p=0.090), it dramatically increased LAD blood flow during diastole (from 62.4±31.4 to 98.3±36.3, p=0.001), resulting in a net significant increase in mean LAD blood flow (from 50.8±23.4 to 64.6±24.2, p=0.034) (FIG. 24, B-D, Table 1). The decrease in systolic LAD blood flow and the dramatic increase in diastolic blood flow mirror the PULVAD-induced changes in aortic blood pressure (i.e., the decrease in systolic pressure and the diastolic pressure augmentation, respectively). These findings are consistent with the notion that in the reperfused ischemic heart (where coronary auto-regulation is severely compromised), perfusion pressure (rather than myocardial oxygen demand) becomes the main determinant of coronary flow.14, 15 In contrast, blood flow in the common carotid remained unaffected by PULVAD support (PULVAD off: 88.0±55.8 vs. PULVAD on: 85.1±56.1, p=0.173), indicating the intact autoregulatory capacity of the cerebral circulation.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

While the disclosed embodiments have been described and depicted in the drawings in the context of the human spine, it should be understood by one of ordinary skill that all or various aspects of the embodiments hereof may be used in in connection with other species and within any species on other parts of the body where deep access within the tissue is desirable.

Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

The invention claimed is:

1. A method for promoting blood flow comprising the steps of:
   (a) preparing a clinical subject for receiving an implantable device wherein the clinical subject has a thoracic cavity that includes a heart having a pericardium, an ascending aorta, a pulmonary artery, a superior vena cava, and left and right lungs;
   (b) providing an implantable pump comprising a blood port and a gas port;
   (c) placing the implantable pump between the heart and the right lung of the clinical subject;
   (d) partially clamping the ascending aorta of the clinical subject;
   (e) providing a graft assembly that comprises a flexible graft conduit that includes a tissue attachment end and a pump attachment end that comprises a washer, and a graft connector;
   (f) affixing the tissue attachment end of the flexible graft conduit to the partially clamped aorta;
   (g) providing a drive line comprising a gas conduit attachable at a first end to the gas port of the implantable pump, the drive line further comprising a sensor conduit and a heart sensor passed therethrough, the heart sensor comprising one or more of a plurality of electrodes and fiber optic sensors, the heart sensor attachable at a first end to the clinical subject, wherein the second end of the gas conduit and a second end of the sensor conduit are attachable to a drive system for delivering gas flow through the drive line gas conduit in response to signals driven by the heart sensor, the drive line including a disc shaped circumferential flange;
   (h) passing the drive line through an incision in the clinical subject with the flange abutting the incision;
   (i) attaching the gas conduit to the gas port of the pump;
   (j) placing each of the one or more of a plurality of electrodes and fiber optic sensors on an anatomical structure of the clinical subject selected from a portion of the pericardium, and within one of the pulmonary artery and the arterial artery;
   (k) connecting the second ends of the conduits of the drive line to the drive system;
   (l) affixing the implantable pump to the graft assembly by engagement between the graft connector and a housing connector on the blood port of the pump;
   (m) removing the clamp from the clinical subject's aorta to permit blood flow from the heart into the implantable pump via the graft and activating the drive system.

2. The method for promoting blood flow according to claim 1 wherein the implantable pump comprises: a rigid housing with an oblate spheroid shape and defining an inner chamber divided by a movable elastomeric membrane into an air sub-chamber which is connectible through the drive line to an external pneumatic source, and a blood sub-chamber which is connectible through a graft assembly to an anatomical heart, the housing including the blood port opening to the blood sub-chamber, the blood port adjacent an upper apex of the housing and oriented at an angle that is in a range from about 0 degrees to about 50 degrees relative to a through axis of the oblate spheroid, the housing also including the gas port opening to the gas sub-chamber, the gas port situated at a lower apex of the housing.

3. The method for promoting blood flow according to claim 2, wherein one or both of the blood port and the gas port comprises an opening that is valveless.

4. The method for promoting blood flow according to claim 2, wherein the elastomeric membrane has a shape that generally conforms to the inner chamber and the blood port and has an expansion volume that is less than a total volume of the chamber and the blood port.

5. The method for promoting blood flow according to claim 2, wherein the blood port is oriented at an angle that is in a range from about 20 degrees to about 50 degrees relative to a through axis of the oblate spheroid.

6. The method for promoting blood flow according to claim 2, further comprising a housing connector and a graft assembly.

7. The method for promoting blood flow according to claim 6, wherein the graft assembly comprises a graft conduit, a washer, and a graft connector.

8. The method for promoting blood flow according to claim 7, wherein the graft connector is engageable with the housing connector by any one of threaded, snap fit, or quick connector.

9. The method for promoting blood flow according to claim 7, each of the blood port and graft conduit having an internal surface, each such internal surface having essentially the same diameter at an interior surface interface therebetween.

10. The method for promoting blood flow according to claim 2, wherein the blood port has a blood port axis that intersects a central axis through the rigid housing at an angle that is from about 35 to about 45 degrees.

11. The method for promoting blood flow according to claim 2, wherein the gas port has an inner diameter in the range from about 1.5 mm to about 2 mm.

12. The method of promoting blood flow according to claim 1, wherein the gas conduit and the sensor conduit are contiguously connected over at least a portion a length of the drive line and are split apart at each of first and second ends of the drive line, the gas conduit being attachable at a first end to the gas port of the implantable pump, the heart sensor monitoring heart rhythm passed through the sensor conduit.

13. The method for promoting blood flow according to claim 1, wherein:
   the implantable pump further comprises: a rigid housing with an oblate spheroid shape and defining an inner chamber divided by a movable elastomeric membrane into an air sub-chamber which is connectible through the drive line to an external pneumatic source, and a blood sub-chamber which is connectible through the graft assembly to an anatomical heart, the housing including the blood port opening to the blood sub-chamber, the blood port adjacent an upper apex of the housing and oriented at an angle that is in a range from about 20 degrees to about 50 degrees relative to a through axis of the oblate spheroid, the housing also including the gas port opening to the gas sub-chamber, the gas port situated at a lower apex of the housing;
   the housing connector is affixed to the blood port, and adapted to engage with the graft assembly; and
   the heart sensor monitors heart rhythm.

14. The method for promoting blood flow according to claim 13, wherein the gas conduit and sensor conduit of the drive line are continuous at their connection to the drive system and are split in two prior to the attachment of the gas conduit to the gas port.

15. The method for promoting blood flow according to claim 13, wherein the sensor is selected from one or more of electrodes and fiber optic sensors.

16. The method for promoting blood flow according to claim 15, wherein the sensor comprises a plurality of electrodes.

17. The method for promoting blood flow according to claim 13, wherein the gas conduit portion of the drive line includes a disc shaped circumferential flange.

18. The method for promoting blood flow according to claim 1, wherein the method does not require the employment of heart lung bypass.

19. The method for promoting blood flow according to claim 18, wherein the blood port of the pump is oriented within the clinical subject's anatomy at angle to allow for anatomical fit and attachment to the ascending aorta while reducing the potential for kinking the graft conduit and superior vena cava compression.

20. The method for promoting blood flow according to claim 1 wherein the implantable pump is a device for assisting blood flow, the device comprising:
  (i) a rigid housing having an oblate spheroid shape and comprising a blood portal section and a gas port section, the blood portal and gas port sections defining within the rigid housing a chamber having an oblate spheroid shape,
    (1) the blood portal section comprising the blood port having a cylindrical shape and defining a through channel between an exterior of the rigid housing and the chamber, the blood portal section having a blood portal axis that intersects a central axis through the blood portal and gas port sections of the rigid housing;
    (2) the gas port section having an interior surface that includes a base, the base comprising a plurality of grooves and the gas port defining a gas flow conduit between the exterior of the rigid housing and the chamber, the gas port having a gas port axis that is normal to the rigid housing axis;
  (ii) an elastomeric membrane comprising a bulb section, a cylindrical neck, and a cuff that interfaces with the housing connector, and having a shape that generally conforms to the chamber and the blood portal section and having an expansion volume that is less than a total volume of the chamber and the blood portal section, wherein the chamber includes a dead volume of from about 3 cc to about 10 cc when the elastomeric membrane is at its maximum expansion volume;
  (iii) a housing connector affixed to the blood portal section, and adapted to engage with a graft assembly; and
  (iv) a graft assembly comprising a graft conduit, a washer, and a graft connector engageable with the housing connector.

* * * * *